United States Patent
Kawasaki et al.

(10) Patent No.: US 8,064,667 B2
(45) Date of Patent: Nov. 22, 2011

(54) X-RAY APPARATUS, IMAGE PROCESSING DISPLAY APPARATUS AND COMPUTER PROGRAM PRODUCT

(75) Inventors: Tomohiro Kawasaki, Otawara (JP); Hitoshi Yamagata, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 760 days.

(21) Appl. No.: 12/170,040

(22) Filed: Jul. 9, 2008

(65) Prior Publication Data

US 2009/0016483 A1    Jan. 15, 2009

(30) Foreign Application Priority Data

Jul. 10, 2007 (JP) .................................. 2007-180761
May 7, 2008 (JP) .................................. 2008-121516

(51) Int. Cl.
*G06K 9/00* (2006.01)
(52) U.S. Cl. ......................... 382/128; 378/98; 378/98.12
(58) Field of Classification Search .................. 382/128, 382/130–132; 378/4–20, 98, 98.11, 98.12
See application file for complete search history.

(56) References Cited

U.S. PATENT DOCUMENTS
7,369,691 B2    5/2008 Kondo et al.

FOREIGN PATENT DOCUMENTS
| CN | 1551033 A | 12/2004 |
| JP | 2004-283373 | 10/2004 |
| JP | 2007-83038 | 4/2007 |

OTHER PUBLICATIONS

U.S. Appl. No. 12/137,144, filed Jun. 11, 2008, Hideaki Kobayashi et al.
U.S. Appl. No. 12/167,561, filed Jul. 3, 2008, Satoshi Wakai et al.

*Primary Examiner* — Courtney Thomas
(74) *Attorney, Agent, or Firm* — Oblon, Spivak, McClelland, Maier & Neustadt, L.L.P.

(57) ABSTRACT

An X-ray imaging machine is configured such that a three-dimensional blood-vessel information creating unit creates information concerning a three-dimensional blood-vessel core line and a position of a plaque in a subject blood vessel based on three-dimensional volume data obtained from an image taken by an X-ray computed tomography apparatus. A plaque-depth information image creating unit creates a plaque-depth information image on which the plaque is differently displayed in accordance with whether the plaque is present in front of or in the back of the three-dimensional blood-vessel core line with respect to a projection direction, based on the created information concerning the three-dimensional blood-vessel core line and the position of the plaque. An X-ray image display unit displays the created plaque-depth information image over an X-ray image in a superimposed manner.

25 Claims, 21 Drawing Sheets

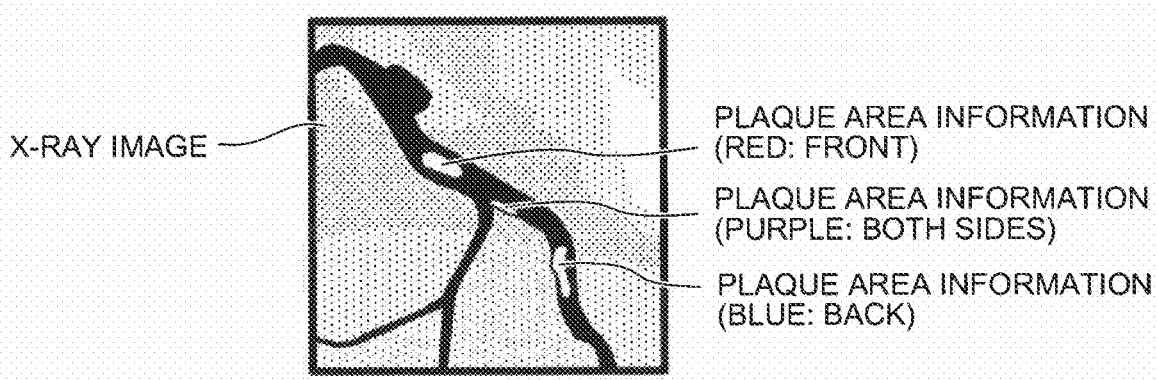
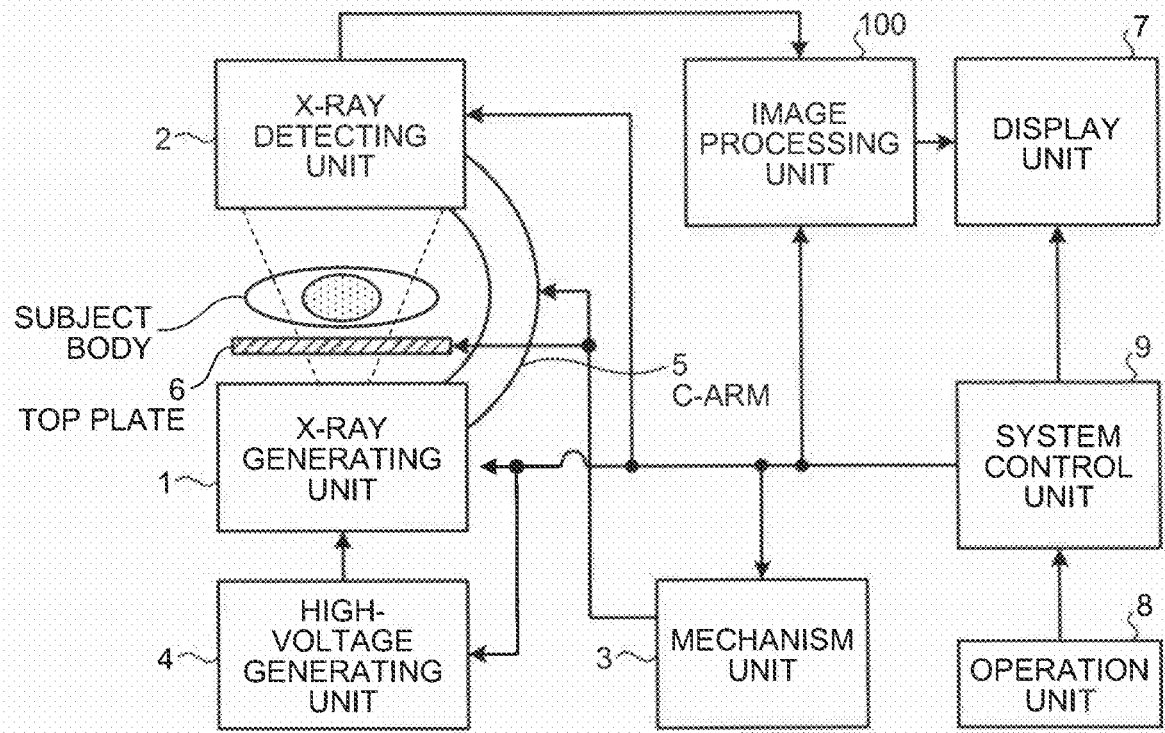

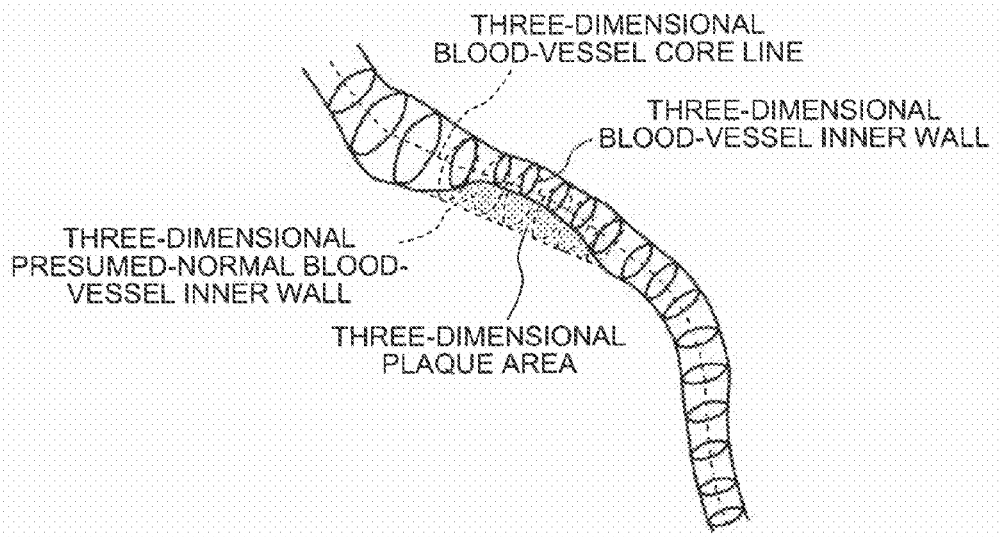
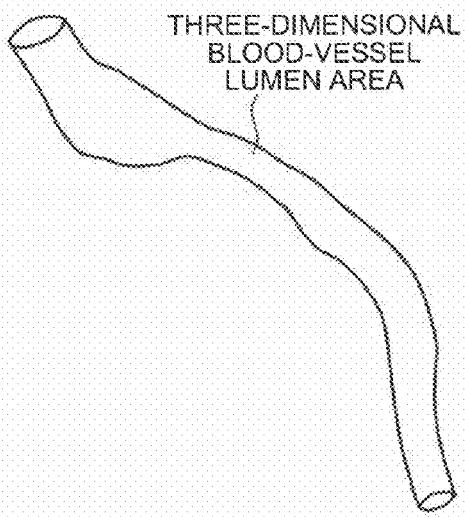
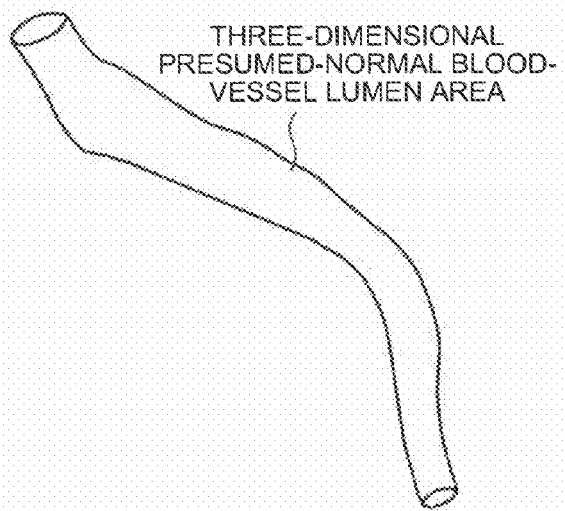

BLOOD-VESSEL RUNNING-
DIRECTION INFORMATION IMAGE

GUIDE-WIRE DIRECTIONAL-
INFORMATION IMAGE

ALARM INDICATION IMAGE

BLOOD-VESSEL RUNNING-
DIRECTION INFORMATION
DISPLAYED X-RAY IMAGE

ARROW INDICATING
HEAD DIRECTION OF
GUIDE WIRE

VIRTUAL ENDOSCOPIC IMAGE

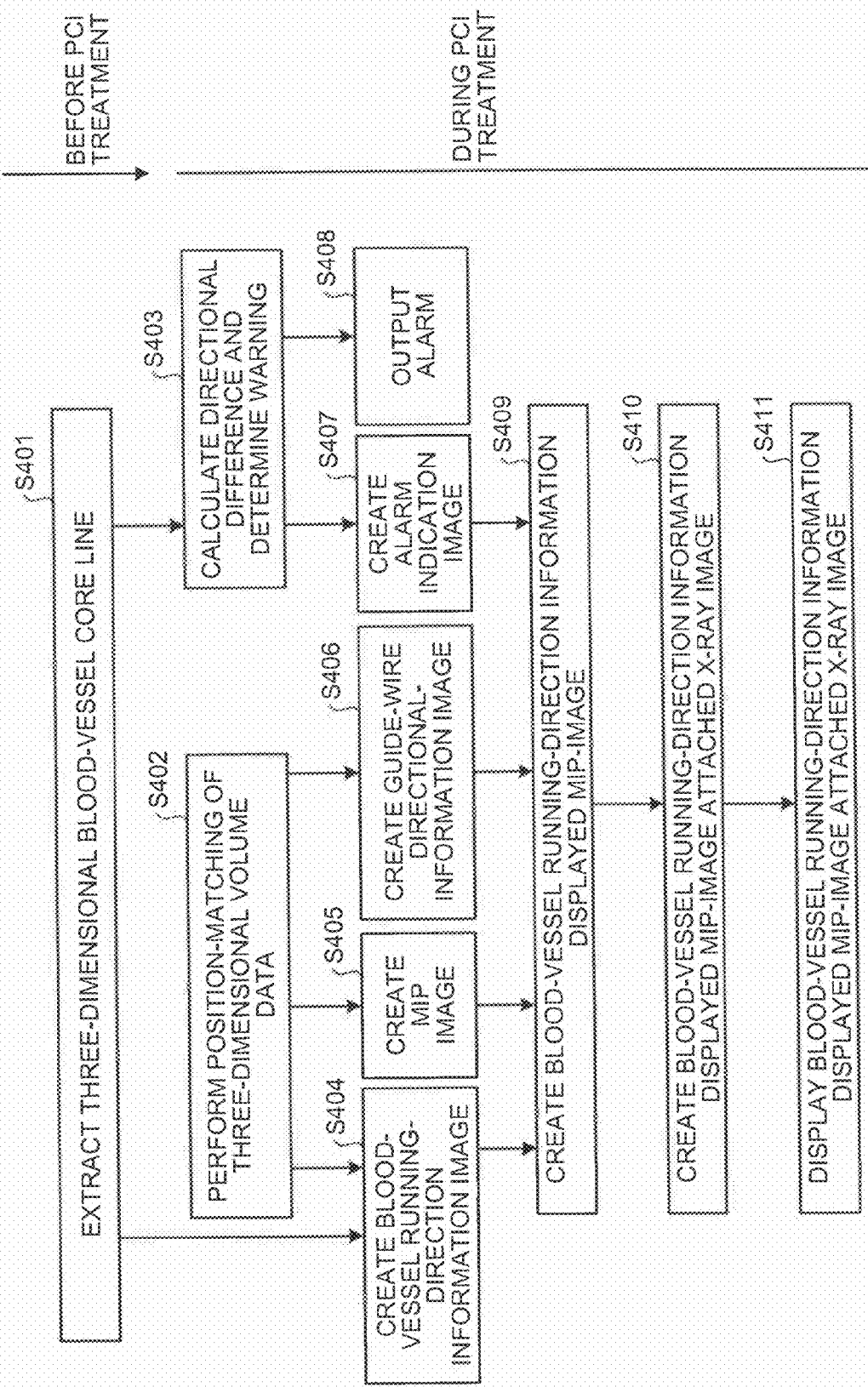

X-RAY APPARATUS, IMAGE PROCESSING DISPLAY APPARATUS AND COMPUTER PROGRAM PRODUCT

CROSS-REFERENCE TO RELATED APPLICATIONS

This application is based upon and claims the benefit of priority from the prior Japanese Patent Application No. 2007-180761, filed on Jul. 10, 2007, and No. 2008-121516, filed on May 7, 2008; the entire contents of which are incorporated herein by reference.

BACKGROUND OF THE INVENTION

1. Field of the Invention

The present invention relates to an X-ray apparatus, such as an X-ray angiographic apparatus, an image processing display apparatus, and a computer program product, and particularly relates to a technology for assisting a treatment that is performed by inserting a linear structure, such as a guide wire, into a blood vessel.

2. Description of the Related Art

Conventionally, there has been a treatment method for expanding a narrowed portion or a blocked portion of a coronary artery by inserting a linear structure, such as a guide wire or a catheter, into a coronary artery of a heart. Such treatment is called as Percutaneous Coronary Intervention (PCI). According to the PCI treatment, an X-ray apparatus, such as an X-ray angiographic apparatus, is used. The X-ray angiographic apparatus displays an X-ray perspective projection image (hereinafter, "X-ray image") during a PCI treatment as a guide image when inserting a guide wire to a lesion-site (coronary artery coarctation).

Moreover, as a method for diagnosing a coronary artery, clinical application software for an X-ray CT apparatus, so-called coronary-artery analysis software has been known (for example, see JP-A 2004-283373 (KOKAI)). The coronary-artery analysis software has a function of obtaining three-dimensional data of a blood-vessel core line, a blood-vessel inner wall, and a presumed-normal blood-vessel inner wall by using three-dimensional volume data of a heart area.

Under the PCI treatment, it is difficult to grasp a lumen form in a coronary-artery coarctation area only by referring to an X-ray image as a guide image, consequently, accuracy of operation may be sometimes decreased in some cases. In such case, an operator is assisted by displaying an image of a coronary-artery inner wall obtained by using the coronary-artery analysis software onto a separate device different from the X-ray angiographic apparatus, or by developing the image onto a film and referring it.

However, it is sometimes difficult to move the guide wire ahead in a blood vessel during a PCI treatment in some cases even by using the coronary-artery analysis software.

For example, when moving the guide wire ahead of a coarctation, the head of the guide wire sometimes comes in contact with a blood-vessel lesion-site (for example, a plaque (such as an arteriosclerotic plaque)) in the coarctation, and the guide wire may not be moved further in the blood vessel in some cases. FIG. 26 is a schematic diagram for explaining relation between the direction of a guide wire and a coarctation. For example, as shown in the upper section of the figure, when a blood-vessel lesion-site is formed on a inner wall of a coronary artery, as the guide wire is turned as shown in the middle section of the figure, the head of the guide wire can be passed through as shown in the lower section of the figure.

However, for example, if the coronary artery is imaged from the direction of an arrow shown in the upper section of the figure, an operator cannot grasp whether the blood-vessel lesion-site is present in front or in the back. In such case, the operator cannot determine to which direction the guide wire is to be turned, and cannot move the guide wire ahead inside the blood vessel.

Moreover, when moving the guide wire to a coarctation, if the head of the guide wire does not face to the running direction of the blood vessel, the head of the guide wire may hit a blood-vessel wall in some cases, consequently the guide wire cannot be moved ahead inside the blood vessel. FIG. 27 is a schematic diagram for explaining relation between the direction of the guide wire and the running direction of a blood vessel. For example, as shown in the left section of the figure, when a blood vessel turns from the front to the back at a forward area of the guide wire, as the guide wire is turned as shown in the middle section of the figure, the guide wire can be moved ahead as shown in the right section of the figure.

However, for example, if the coronary artery is imaged from the direction of an arrow shown in the left section of the figure, the operator cannot grasp whether the running direction of the blood-vessel goes to the front or the back. In such case, similarly, the operator cannot determine to which direction the guide wire is to be turned, and cannot move the guide wire ahead inside the blood vessel.

Primarily to avoid such situation, the coronary-artery analysis software is used. However, according to the conventional technology, as described above, because the image of the coronary artery is displayed on a separate device, or developed on a film to be referred, it is difficult to grasp relation between the X-ray image and the position and the direction of the blood vessel. Furthermore, during a treatment, because the operator is operating the guide wire while watching the X-ray image, the operator has no time to see a separate image. Thus, the conventional technology cannot assist the operator sufficiently in some cases.

SUMMARY OF THE INVENTION

According to one aspect of the present invention, an X-ray imaging apparatus includes an X-ray image taking unit that takes an X-ray image by irradiating an X-ray to a subject and detecting the X-ray passed through the subject; a three-dimensional blood-vessel information creating unit that creates information concerning positions of a three-dimensional blood-vessel core line and a blood-vessel lesion-site inside a blood vessel to be imaged, based on three-dimensional volume data obtained from an image taken by a medical diagnostic imaging apparatus; a blood-vessel lesion-site-depth information image creating unit that creates a blood-vessel lesion-site-depth information image in which a display pattern of a blood-vessel lesion-site is changed in accordance with whether the blood-vessel lesion-site is present in front of or in the back of a three-dimensional blood-vessel core line, based on the information concerning positions of the three-dimensional blood-vessel core line and the blood-vessel lesion-site created by the three-dimensional blood-vessel-information creating unit; and an X-ray image display unit that displays the blood-vessel lesion-site-depth information image created by the blood-vessel lesion-site-depth information image creating unit in a superimposed manner over the X-ray image.

According to another aspect of the present invention, an image processing display apparatus includes a three-dimensional blood-vessel information creating unit that creates information concerning positions of a three-dimensional blood-vessel core line and a blood-vessel lesion-site inside a blood vessel to be imaged, based on three-dimensional volume data obtained from an image taken by a medical diagnostic imaging apparatus; a blood-vessel lesion-site-depth information image creating unit that creates a blood-vessel lesion-site-depth information image in which a display pattern of a blood-vessel lesion-site is changed in accordance with whether the blood-vessel lesion-site is present in front of or in the back of a three-dimensional blood-vessel core line, based on the information concerning positions of the three-dimensional blood-vessel core line and the blood-vessel lesion-site created by the three-dimensional blood-vessel-information creating unit; and an X-ray image display unit that displays the blood-vessel lesion-site-depth information image created by the blood-vessel lesion-site-depth information image creating unit in a superimposed manner over an X-ray image taken by an X-ray image taking unit.

According to still another aspect of the present invention, a computer program product having a computer readable medium including programmed instructions for performing an image processing and image display, wherein the instructions, when executed by a computer, cause the computer to perform creating information concerning positions of a three-dimensional blood-vessel core line and a blood-vessel lesion-site inside a blood vessel to be imaged, based on three-dimensional volume data obtained from an image taken by a medical diagnostic imaging apparatus; creating a blood-vessel lesion-site-depth information image in which a display pattern of a blood-vessel lesion-site is changed in accordance with whether the blood-vessel lesion-site is present in front of or in the back of a three-dimensional blood-vessel core line, based on the created information concerning positions of the three-dimensional blood-vessel core line and the blood-vessel lesion-site; and displaying on a display unit the created blood-vessel lesion-site-depth information image in a superimposed manner over an X-ray image taken by an X-ray image taking unit.

According to still another aspect of the present invention, an X-ray imaging apparatus includes an X-ray image taking unit that takes an X-ray image by irradiating an X-ray to a subject and detecting X-ray passed through the subject; a three-dimensional blood-vessel core-line creating unit that creates a three-dimensional blood-vessel core line representing a core line of a blood vessel to be imaged, based on three-dimensional volume data obtained from an image taken by a medical diagnostic imaging apparatus; a blood-vessel running-direction information image creating unit that creates a blood-vessel running-direction information image in which a display pattern of a blood vessel is changed so as to display a running direction of the blood vessel, based on positional information concerning the three-dimensional blood-vessel core line created by the three-dimensional blood-vessel core-line creating unit; and an X-ray image display unit that displays the blood-vessel running-direction information image created by the blood-vessel running-direction information image creating unit in a superimposed manner over the X-ray image.

According to still another aspect of the present invention, an image processing display apparatus includes a three-dimensional blood-vessel core-line creating unit that creates a three-dimensional blood-vessel core line representing a core line of a blood vessel to be imaged, based on three-dimensional volume data obtained from an image imaged by a medical diagnostic imaging apparatus; a blood-vessel running-direction information image creating unit that creates a blood-vessel running-direction information image in which a display pattern of a blood vessel is changed so as to display a running direction of the blood vessel, based on positional information concerning the three-dimensional blood-vessel core line created by the three-dimensional blood-vessel core-line creating unit; and an X-ray image display unit that displays the blood-vessel running-direction information image created by the blood-vessel running-direction information image creating unit in a superimposed manner over an X-ray image taken by an X-ray image taking unit.

According to still another aspect of the present invention, a computer program product having a computer readable medium including programmed instructions for performing an image processing and image display, wherein the instructions, when executed by a computer, cause the computer to perform creating a three-dimensional blood-vessel core line representing a core line of a blood vessel to be imaged based on three-dimensional volume data obtained from an image taken by a medical diagnostic imaging apparatus; creating a blood-vessel running-direction information image in which a display pattern of a blood vessel is changed so as to display a running direction of the blood vessel, based on positional information concerning the created three-dimensional blood-vessel core line; and displaying the created blood-vessel running-direction information image in a superimposed manner over an X-ray image.

BRIEF DESCRIPTION OF THE DRAWINGS

FIG. 1 is a schematic diagram for explaining a concept of depth information display performed by an X-ray angiographic apparatus according to a first embodiment of the present invention;

FIG. 2 is a functional block diagram of a configuration of the X-ray angiographic apparatus according to the first embodiment;

FIGS. 4A to 4C are schematic diagrams illustrating an example of a blood-vessel core line, a blood-vessel inner wall, a presumed normal-blood-vessel inner-wall, and a plaque area in a coronary artery;

FIG. 22 is a flowchart of a processing procedure of the image processing unit according to the fourth embodiment;

DETAILED DESCRIPTION OF THE INVENTION

Figure 3:
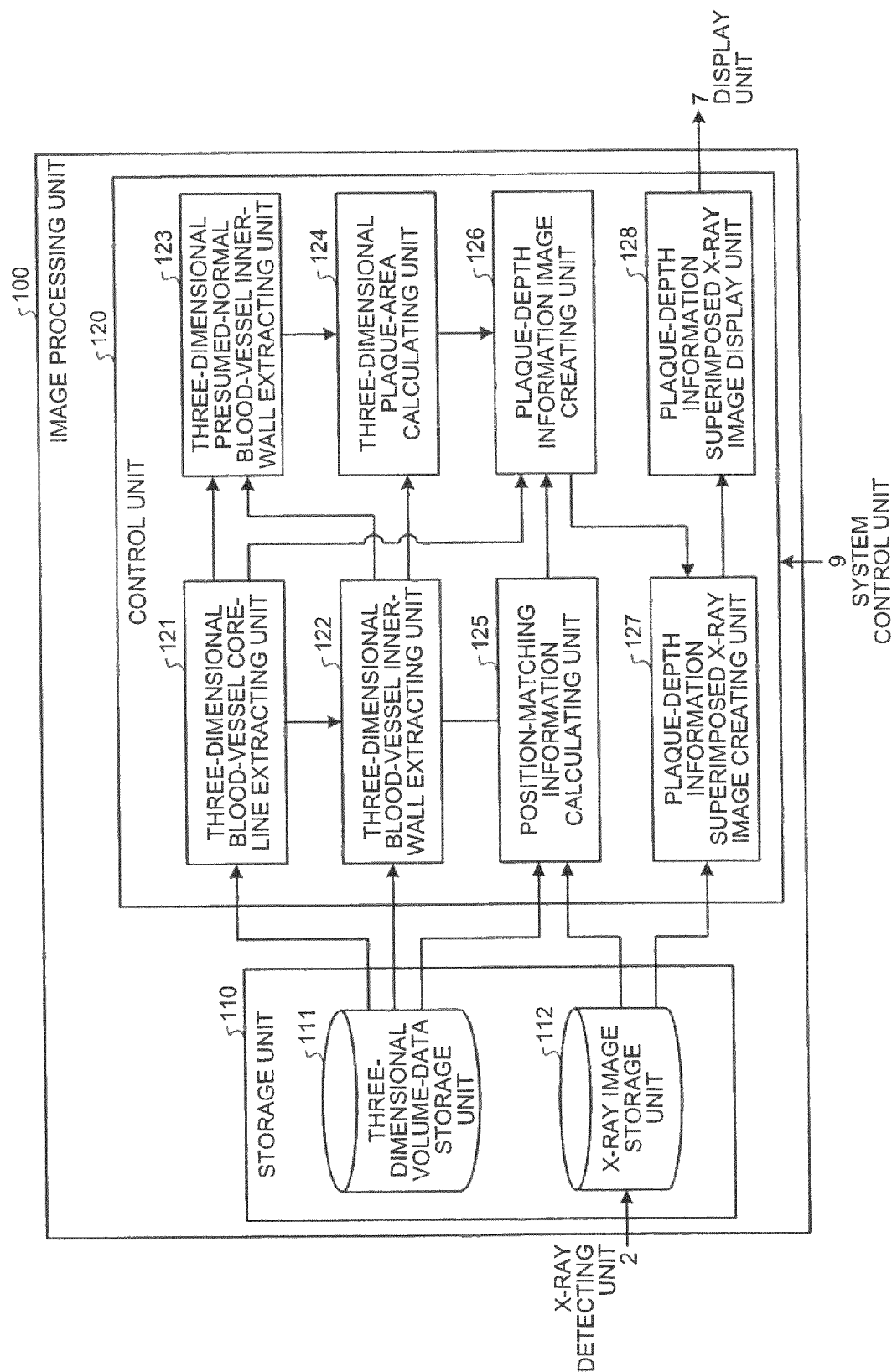
FIG. 3 is a functional block diagram of a configuration of an image processing unit according to the first embodiment.

Exemplary embodiments of an X-ray imaging apparatus, an image-processing display apparatus, and a computer program product according to the present invention will be explained below in detail with reference to the accompanying drawings. The following description explains in a case where the embodiments of the present invention are applied to an X-ray angiographic apparatus that performs an X-ray imaging of a blood vessel, such as a coronary artery. Moreover, the following embodiments are explained about a plaque (arteriosclerotic plaque) as an example of a blood-vessel lesion-site occurring in a blood vessel; however, the embodiments can be applied to other types of blood-vessel lesion-sites.

First of all, a concept of depth information display performed by an X-ray angiographic apparatus according to a first embodiment of the present invention is explained below. FIG. 1 is a schematic diagram for explaining a concept of depth information display performed by the X-ray angiographic apparatus according to the first embodiment. The X-ray angiographic apparatus according to the first embodiment creates, prior to a Percutaneous Coronary Intervention (PCI) treatment, information about the positions of a three-dimensional blood-vessel core line and a plaque in a blood vessel to be imaged based on three-dimensional volume data (three-dimensional image data) obtained from a computed tomography (CT) image imaged in advance by an X-ray CT apparatus.

On the other hand, during the PCI treatment, the X-ray angiographic apparatus creates an image of plaque area information of which display pattern is changed in accordance with whether the plaque is present in front of or in the back of the three-dimensional blood-vessel core line with respect to a projection direction, based on the information about the positions of the three-dimensional blood-vessel core line and the plaque created before the treatment. Specifically, as shown in the figure, when the plaque is present in front of the three-dimensional blood-vessel core line, the X-ray angiographic apparatus creates a red image of the plaque area information, by contrast, when the plaque is present in the back of the three-dimensional blood-vessel core line, the X-ray angiographic apparatus creates a blue image of the plaque area information. The X-ray angiographic apparatus then displays, as shown in FIG. 1, the created image of plaque-area information in a superimposed manner over an X-ray image of a blood vessel under operation of the treatment after performing position-matching. When displaying the image, if plaques are present on the both sides, namely, the front and the back, an image of the plaque area information in an overlap area is displayed in purple.

In this way, the X-ray angiographic apparatus according to the first embodiment has a main feature configured to display during a PCI treatment an image of plaque area information of which display pattern (color, in this case) is changed in accordance with whether the plaque is present in front of or in the back of a blood-vessel core line, in a superimposed manner over an X-ray image of a blood vessel under operation of the treatment. According to the feature, the X-ray angiographic apparatus according to the first embodiment can determine to which direction a guide wire is to be turned by grasping the position of a coarctation, and can move a guide wire forward in a blood vessel without damaging a plaque.

A configuration of the X-ray angiographic apparatus according to the first embodiment is explained below. FIG. 2 is a functional block diagram of a configuration of the X-ray angiographic apparatus according to the first embodiment. As shown in the figure, the X-ray angiographic apparatus includes an X-ray generating unit 1, an X-ray detecting unit 2, a mechanism unit 3, a high-voltage generating unit 4, a C-arm 5, a top plate 6, an image processing unit 100, a display unit 7, an operation unit 8, and a system control unit 9.

The X-ray generating unit 1 is a device that generates X-rays to be irradiated onto a subject body on the top plate 6, and includes an X-ray tube and an X-ray beam limiting device. The X-ray tube generates X-rays by using a high voltage supplied from the high-voltage generating unit 4. The X-ray beam limiting device controls an X-ray field by shielding part of an X-ray generated by the X-ray tube.

The X-ray detecting unit 2 is a device that detects an X-ray passed through the subject body and creates X-ray image data, and includes a plane surface detector that detects an X-ray, a gate driver that takes out an electric charge from the plane surface detector, an electric charge-voltage converter that converts the electric charge taken out by the gate driver to a voltage, and an analog to digital (A/D) converter that converts the voltage converted by the electric charge-voltage converter to a digital value.

The mechanism unit 3 is a device that moves the C-arm 5 and the top plate 6, and includes a C-arm rotating-moving mechanism that rotates and moves the C-arm 5, and a top-plate moving mechanism that moves the top plate 6, and a mechanism control unit that controls the C-arm rotating-moving mechanism and the top-plate moving mechanism based on an instruction from the system control unit 9.

The high-voltage generating unit 4 is a device that supplies a high voltage required for the X-ray generating unit 1 to generate X-rays, and includes an X-ray control unit that controls generation of an X-ray by controlling generation of a high voltage based on an instruction from the system control unit 9, and a high-voltage generator that generates a high voltage. The C-arm 5 is an arm that holds the X-ray generating unit 1 and the X-ray detecting unit 2. The top plate 6 is a plate on which a subject body is placed.

The display unit 7 is a device that displays thereon various images, such as an X-ray image, and includes a monitor that displays thereon an image, and a display control unit that controls display to the monitor. The operation unit 8 includes a mouse, a keyboard, and a joystick, and is configured to receive an operation by an operator. The system control unit 9 is a device that controls the whole of the X-ray angiographic apparatus based on an operation by an operator.

The image processing unit 100 is a processing unit that creates an X-ray image based on X-ray image data created by the X-ray detecting unit 2. FIG. 3 is a functional block diagram of a configuration of the image processing unit 100 according to the first embodiment. As shown in the figure, the image processing unit 100 includes a storage unit 110 and a control unit 120.

The storage unit 110 stores therein data and a program required for the control unit 120 to perform various processing, and includes a three-dimensional volume-data storage unit 111 and an X-ray image storage unit 112, which are relevant to the present invention.

The three-dimensional volume-data storage unit 111 stores therein three-dimensional volume data of an image of a heart area imaged by performing coronary imaging with an X-ray CT apparatus. It is assumed that the three-dimensional volume-data storage unit 111 stores therein, prior to a PCI treatment, three-dimensional volume data of an image imaged in advance by the X-ray CT apparatus.

The X-ray image storage unit 112 stores therein an X-ray image of a heart area imaged by the X-ray angiographic apparatus. It is assumed that images are collected in real-time with regular intervals during a PCI treatment, and stored in the X-ray image storage unit 112. If an X-ray image is imaged by Image Intensifier (I. I.), a deformation of an image of I. I. needs to be corrected in real time.

The control unit 120 controls processing of X-ray image data received from the X-ray detecting unit 2, under the control of the system control unit 9. As units relevant to the present invention, the control unit 120 includes a three-dimensional blood-vessel core-line extracting unit 121, a three-dimensional blood-vessel inner-wall extracting unit 122, a three-dimensional presumed normal-blood-vessel inner-wall extracting unit 123, a three-dimensional plaque-area calculating unit 124, a position-matching information calculating unit 125, a plaque-depth information image creating unit 126, a plaque-depth information superimposed X-ray image creating unit 127, and a plaque-depth information superimposed X-ray image display unit 128.

The three-dimensional blood-vessel core-line extracting unit 121 creates data that represents a core line of a coronary artery on which a PCI treatment is to be performed (hereinafter, "three-dimensional blood-vessel core-line data"), based on CT values of three-dimensional volume data stored in the three-dimensional volume-data storage unit 111. FIGS. 4A to 4C are schematic diagrams that depict an example of a blood-vessel core line, a blood-vessel inner wall, a presumed normal-blood-vessel inner-wall, and a plaque area in a coronary artery.

For example, the three-dimensional blood-vessel core-line extracting unit 121 creates three-dimensional blood-vessel core-line data that represents a blood-vessel core line, for example, the three-dimensional blood-vessel core line shown in FIG. 4A. The three-dimensional blood-vessel core-line data is created as three-dimensional point-series data, of which a data structure and a creation algorithm uses a data structure and a creation algorithm according to a known technology, such as the technology described in JP-A 2004-283373 (KOKAI).

The three-dimensional blood-vessel inner-wall extracting unit 122 creates data that represents data related to a blood-vessel inner wall around the blood-vessel core line (hereinafter, "three-dimensional blood-vessel inner-wall data"), based on CT values of three-dimensional volume data stored in the three-dimensional volume-data storage unit 111, and a three-dimensional blood-vessel core line created by the three-dimensional blood-vessel core-line extracting unit 121.

For example, the three-dimensional blood-vessel inner-wall extracting unit 122 creates three-dimensional blood-vessel inner-wall data that represents a blood-vessel inner wall, for example, the three-dimensional blood-vessel inner wall shown in FIG. 4A. The three-dimensional blood-vessel inner-wall data is created as three-dimensional point-series data, of which a data structure and a creation algorithm uses a data structure and a creation algorithm according to a known technology, such as the technology described in JP-A 2004-283373 (KOKAI).

The three-dimensional presumed normal-blood-vessel inner-wall extracting unit 123 creates data that represents a presumed normal-blood-vessel inner-wall around the blood-vessel core line (hereinafter, "three-dimensional presumed normal-blood-vessel inner-wall data"), based on three-dimensional blood-vessel core-line data created by the three-dimensional blood-vessel core-line extracting unit 121, and three-dimensional blood-vessel inner-wall data created by the three-dimensional blood-vessel inner-wall extracting unit 122.

For example, the three-dimensional presumed normal-blood-vessel inner-wall extracting unit 123 creates three-dimensional presumed normal-blood-vessel inner-wall data that represents a presumed normal-blood-vessel inner-wall, for example, the three-dimensional blood-vessel inner wall shown in FIG. 4A. The three-dimensional presumed normal-blood-vessel inner-wall data is created as three-dimensional point-series data, of which a data structure and a creation algorithm uses a data structure and a creation algorithm according to a known technology, such as the technology described in JP-A 2004-283373 (KOKAI).

The three-dimensional plaque-area calculating unit 124 calculates data that represents an area in which a plaque is formed (a plaque area) (hereinafter, "three-dimensional plaque-area data"), based on three-dimensional blood-vessel inner-wall data created by the three-dimensional blood-vessel inner-wall extracting unit 122, and three-dimensional presumed normal-blood-vessel inner-wall data created by the three-dimensional presumed normal-blood-vessel inner-wall extracting unit 123.

For example, the three-dimensional plaque-area calculating unit 124 calculates three-dimensional plaque-area data that represents a plaque area, for example, the three-dimensional plaque area shown in FIG. 4A. Specifically, the three-dimensional plaque-area calculating unit 124 calculates as a plaque area, for example, a differential area between a three-dimensional blood-vessel lumen area (see FIG. 4B) that is calculated from three-dimensional blood-vessel inner-wall data, and a three-dimensional presumed-normal blood-vessel lumen area (see FIG. 4C) that is calculated from three-dimensional presumed normal-blood-vessel inner-wall data.

The position-matching information calculating unit 125 acquires position-matching parameters from three-dimensional volume data stored in the three-dimensional volume-data storage unit 111, namely, a projection direction, a position, and a magnification, which are parameters to be required for creating an image having the same projection direction, position, and magnification as those of an X-ray image stored in the X-ray image storage unit 112.

It is assumed that the position-matching information calculating unit 125 acquires position-matching parameters from the system control unit 9. It is assumed that a coordinate system that is a reference of the acquired projection direction, position, and magnification is equal to a coordinate system that is a reference of parameters acquired as additional information of an X-ray CT image, or can be converted one-to-one.

Figure 5:
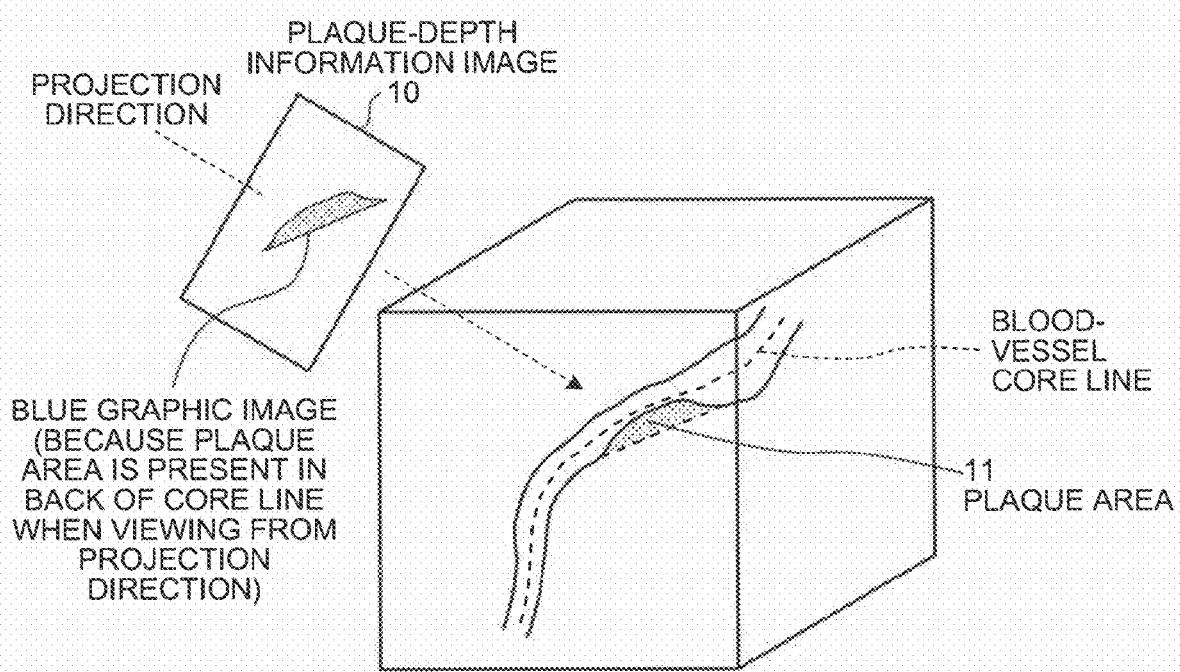
FIG. 5 is a schematic diagram for explaining a method of creating a plaque-depth information image.

The plaque-depth information image creating unit 126 creates a plaque-depth information image based on three-dimensional blood-vessel core-line data created by the three-dimensional blood-vessel core-line extracting unit 121, three-dimensional plaque-area data calculated by the three-dimensional plaque-area calculating unit 124, and position-matching parameters (projection direction, position, and magnification) acquired by the position-matching information calculating unit 125. FIG. 5 is a schematic diagram for explaining a method of creating a plaque-depth information image. The figure depicts an example where a plaque area is present in the back of the three-dimensional blood-vessel core line with respect to the projection direction.

Specifically, as shown in the figure, the plaque-depth information image creating unit 126 creates as a plaque-depth information image 10 a two-dimensional graphic image that is projected from a plaque area 11 represented by three-dimensional plaque-area data calculated by the three-dimensional plaque-area calculating unit 124 in accordance with position-matching parameters acquired by the position-matching information calculating unit 125.

When creating the image, the plaque-depth information image creating unit 126 creates the plaque-depth information image 10 such that the plaque area 11 present in front of the three-dimensional blood-vessel core line in the projection direction is in red, the plaque area 11 present in the back of the three-dimensional blood-vessel core line is in blue, and the other areas are colorless.

The plaque-depth information image 10 is a 32-bit color Red-Green-Blue-Alpha (RGBA) image, and created such that an alpha value (A value) that indicates transparency of the plaque area is to be 255 (opaque), an A value of the other areas is to be zero (transparent). If the plaque areas 11 are present both in front and the back of the three-dimensional blood-vessel core line, the color of an area where the both of the plaque areas 11 overlap is synthesized and turned to purple.

Figure 6:
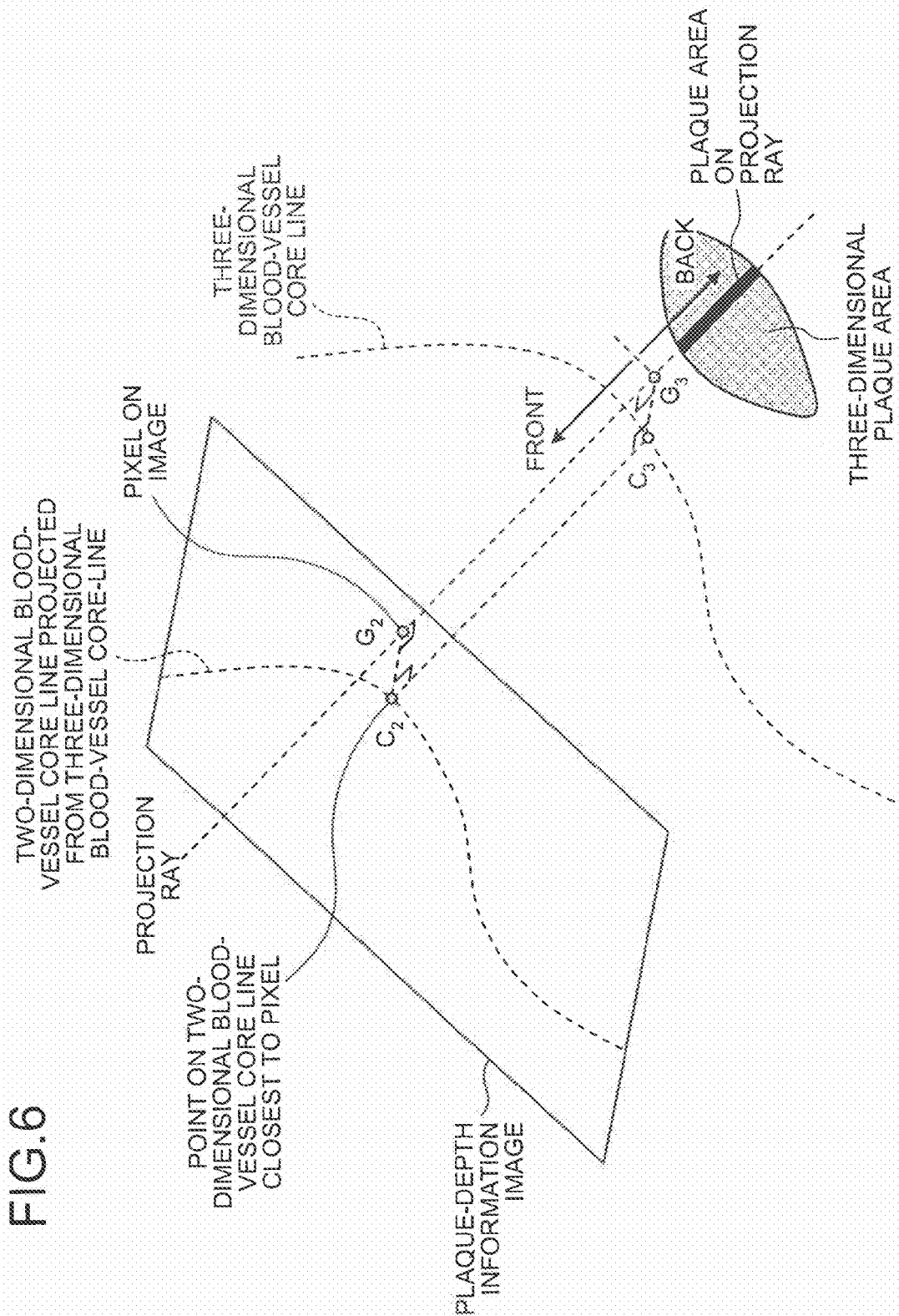
FIG. 6 is a schematic diagram for explaining position determination of a plaque area.

A method of determining whether a plaque area is present in front of or in the back of the blood-vessel core line with respect to the projection direction is explained below. FIG. 6 is a schematic diagram for explaining position determination of a plaque area. The figure depicts an example where a plaque area is present in the back of the three-dimensional blood-vessel core line.

For example, as shown in the figure, a pixel $G_2$, which is a pixel on a plaque-depth information image, is considered. First of all, a distance is calculated between a point $C_2$ on a two-dimensional blood-vessel core line closest to the pixel $G_2$ on the plaque-depth information image, and a point $C_3$ on the three-dimensional blood-vessel core line corresponding to the point $C_2$. Subsequently, a point is moved from the pixel $G_2$ along a projection ray by the same distance as the calculated distance to a position, which is denoted as a point $G_3$.

Then, it is determined whether the plaque area on the projection ray is present in front of or in the back of the point $G_3$, and based on a determination result, it is determined whether the pixel $G_2$ indicates a plaque area present in front of the blood-vessel core line with respect to the projection direction, or a plaque area present in the back of the blood-vessel core line. In other words, if the plaque area is present in front of the point $G_3$, the color of the pixel $G_2$ is to be in red, by contrast, if it is present in the back, the color of the pixel $G_2$ is to be in blue.

It can be configured such that colors of a plaque area on a plaque-depth information image when the plaque area is present in front of the blood-vessel core line and when the plaque area is present in the back of the blood-vessel core line can be set by a user by arbitrarily setting a color (Red-Green-Blue (RGB) values) and transparency (A value).

Moreover, it can be configured to draw additionally an image on which three-dimensional blood-vessel core-line data created by the three-dimensional blood-vessel core-line extracting unit 121 and three-dimensional blood-vessel inner-wall data created by the three-dimensional blood-vessel inner-wall extracting unit 122 are projected in accordance with position-matching parameters acquired by the position-matching information calculating unit 125. Accordingly, even when the created X-ray image is deviated more or less from the position according to the plaque-depth information on the plaque-depth information image, corresponding relation can be easily grasped.

The plaque-depth information superimposed X-ray image creating unit 127 acquires an X-ray image stored in the X-ray image storage unit 112, and creates a two-dimensional image on which a plaque-depth information image created by the plaque-depth information image creating unit 126 is superimposed over the acquired X-ray image (hereinafter, "plaque-depth information superimposed X-ray image").

For example, the plaque-depth information superimposed X-ray image creating unit 127 creates a plaque-depth information superimposed X-ray image shown in FIG. 1. When creating such plaque-depth information superimposed image, the plaque-depth information superimposed X-ray image creating unit 127 converts an 8-bit X-ray image into a 24-bit color (RGB) image to synthesize a 32-bit color image of the plaque-depth information image.

The plaque-depth information superimposed X-ray image display unit 128 displays a plaque-depth information superimposed X-ray image created by the plaque-depth information superimposed X-ray image creating unit 127 onto the display unit 7.

Figure 7:
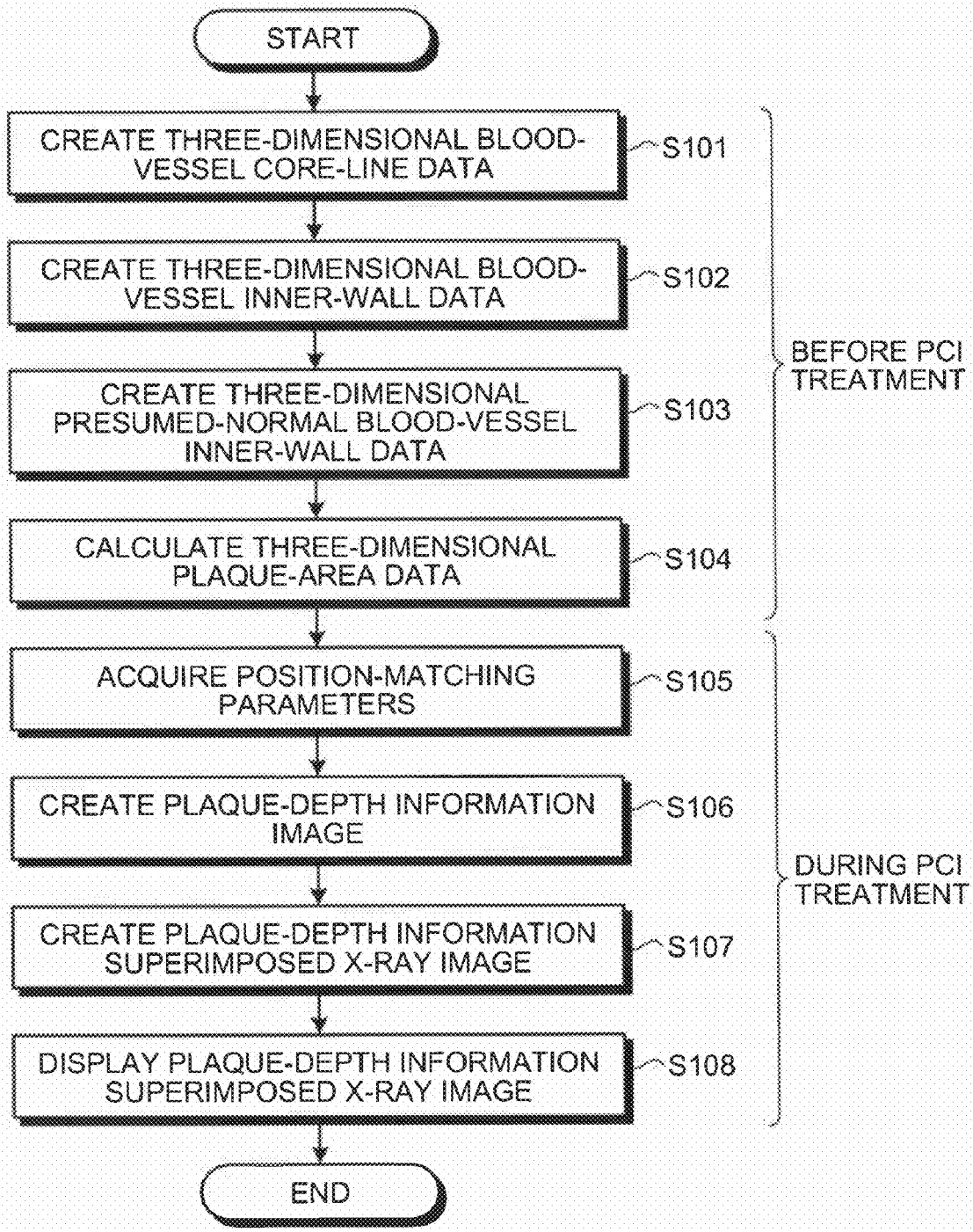
FIG. 7 is a flowchart of a processing procedure of the image processing unit according to the first embodiment.

A processing procedure of the image processing unit 100 according to the first embodiment is explained below. FIG. 7 is a flowchart of the processing procedure of the image processing unit 100 according to the first embodiment. As shown in the figure, according to the image processing unit 100, prior to a PCI treatment, to begin with, the three-dimensional blood-vessel core-line extracting unit 121 creates three-dimensional blood-vessel core-line data of a coronary artery on which the PCI treatment is to be performed based on CT values of three-dimensional volume data stored in the three-dimensional volume-data storage unit 111 (Step S101).

Subsequently, the three-dimensional blood-vessel inner-wall extracting unit 122 creates three-dimensional blood-vessel inner-wall data around the blood-vessel core line based on the CT values of three-dimensional volume data stored in the three-dimensional volume-data storage unit 111, and the three-dimensional blood-vessel core line created by the three-dimensional blood-vessel core-line extracting unit 121 (Step S102).

Further subsequently, the three-dimensional presumed normal-blood-vessel inner-wall extracting unit 123 creates three-dimensional presumed normal-blood-vessel inner-wall data around the blood-vessel core line based on the three-dimensional blood-vessel core-line data created by the three-dimensional blood-vessel core-line extracting unit 121, and the three-dimensional blood-vessel inner-wall data created by the three-dimensional blood-vessel inner-wall extracting unit 122 (Step S103).

After that, the three-dimensional plaque-area calculating unit 124 calculates three-dimensional plaque-area data based on the three-dimensional blood-vessel inner-wall data created by the three-dimensional blood-vessel inner-wall extracting unit 122, and the three-dimensional presumed normal-blood-vessel inner-wall data created by the three-dimensional presumed normal-blood-vessel inner-wall extracting unit 123 (Step S104).

During the PCI treatment, the position-matching information calculating unit 125 acquires position-matching parameters from three-dimensional volume data stored in the three-dimensional volume-data storage unit 111, namely, the projection direction, the position, and the magnification, which are parameters to be required for creating an image having the same projection direction, position, and magnification as those of the X-ray image stored in the X-ray image storage unit 112 (Step S105).

Subsequently, the plaque-depth information image creating unit 126 creates a plaque-depth information image based on the three-dimensional blood-vessel core-line data created by the three-dimensional blood-vessel core-line extracting unit 121, the three-dimensional plaque-area data calculated by the three-dimensional plaque-area calculating unit 124, and the position-matching parameters acquired by the position-matching information calculating unit 125 (Step S106).

Further subsequently, the plaque-depth information superimposed X-ray image creating unit 127 acquires the X-ray image stored in the X-ray image storage unit 112, and creates a plaque-depth information superimposed X-ray image that the plaque-depth information image created by the plaque-depth information image creating unit 126 is superimposed over the acquired X-ray image (Step S107).

The plaque-depth information superimposed X-ray image display unit 128 then displays the plaque-depth information superimposed X-ray image created by the plaque-depth information superimposed X-ray image creating unit 127 onto the display unit 7 (Step S108).

As described above, according to the first embodiment, prior to a PCI treatment, based on three-dimensional volume data obtained from an image imaged by an X-ray CT apparatus, the three-dimensional blood-vessel core-line extracting unit 121 creates three-dimensional blood-vessel core-line data, the three-dimensional blood-vessel inner-wall extracting unit 122 creates three-dimensional blood-vessel inner-wall data, the three-dimensional presumed normal-blood-vessel inner-wall extracting unit 123 creates three-dimensional presumed normal-blood-vessel inner-wall data, and the three-dimensional plaque-area calculating unit 124 creates three-dimensional plaque-area data.

During the PCI treatment, the position-matching information calculating unit 125 calculates position-matching parameters, namely, the projection direction, the position, and the magnification, which are to be required for creating an image having the same projection direction, position, and magnification as those of the X-ray image. Subsequently, the plaque-depth information image creating unit 126 creates a plaque-depth information image on which the plaque is differently displayed in accordance with whether the plaque is present in front of or in the back of the three-dimensional blood-vessel core line with respect to the projection direction.

Further subsequently, the plaque-depth information superimposed X-ray image creating unit 127 creates a plaque-depth information superimposed X-ray image by superimposing the plaque-depth information image over the X-ray image. After that, the plaque-depth information superimposed X-ray image display unit 128 displays the plaque-depth information superimposed X-ray image onto the display unit 7.

Thus, according to the above configuration, the first embodiment is configured such that by displaying information about depth, when an operator moves a guide wire forward inside a blood vessel, the operator can easily determine an appropriate turning direction of the guide wire. Moreover, the X-ray angiographic apparatus can assist the operator to move the guide wire forward inside a blood vessel without damaging a plaque.

Moreover, the first embodiment is configured such that a plaque area present in front of the blood-vessel core line is displayed in red, a plaque area present in the back of the blood-vessel core line is displayed in blue, and when plaque areas are present on the both sides, namely, in the front and the back of the blood-vessel core line, an overlap area of the plaque areas is displayed in purple. However, the present invention is not limited to these. For example, a depth of a color in a plaque area can be changed in accordance with a length in the depth direction of the plaque area.

In such case, specifically, the plaque-depth information image creating unit 126 changes the depth of a display color in the plaque area in accordance with a length in the depth direction of the plaque area on the projection ray shown in FIG. 6 (the length of the black thick line on the three-dimensional plaque area in the figure). As the depth of a display color, for example, when the plaque area is present in the front, an R value is varied within a range of (R, G, B)=(0 to 255, 0, 0); when the plaque area is present in the back, a B value is varied within a range of (R, G, B)=(0, 0, 0 to 255); and when the plaque area is present on the both sides, the R value and the B value in an overlap area are varied within a range of a range of (R, G, B)=(0 to 255, 0, 0 to 255). When changing the color value, a target value of a color is calculated as, for example, 255×length of plaque area [mm]/3 mm, because the thickness of a coronary artery is approximately three millimeters.

Moreover, although according to the first embodiment, it is configured such that a plaque-depth information image including a colored plaque area is constantly displayed as superimposed over an X-ray image, the present invention is not limited to this, and it can be configured such that a plaque-depth information image is displayed only for a certain time period.

In such case, the image processing unit 100 receives an instruction from a user by using a mechanical button or a Graphical User Interface (GUI) displayed on a screen of a display device, and displays the plaque-depth information image over the X-ray image in a superimposed manner only while the button is being pressed. Alternatively, the image processing unit 100 can be configured to receive an instruction from a user by using a button that can switch ON/OFF, and to display a plaque-depth information image over an X-ray image in a superimposed manner only while the button is ON. In this way, the plaque-depth information image can be displayed only during the time period required by the user by displaying the plaque-depth information image based on an instruction from the user.

Alternatively, the image processing unit 100 can be configured to display an plaque-depth information image over an X-ray image in a superimposed manner after performing position-matching, only while displaying an X-ray image in the same heartbeat phase (for example, telediastolic phase) as that of three-dimensional volume data. If the heartbeat phase of the X-ray image is different from the heartbeat phase of the three-dimensional volume data, it is conceivable that accuracy of position-matching of the plaque-depth information image is decreased, consequently the position of the plaque area is deviated with respect to the blood vessel on the X-ray image. However, by displaying a plaque-depth information image only while the heartbeat phases match each other as described above, it can be configured to display the plaque-depth information image only when the position of the plaque area is not deviated with respect to the blood vessel.

In this way, as the image processing unit 100 displays a plaque-depth information image when a user requires it, or only when positioning is performed with a high degree of accuracy, visibility of an X-ray image during a PCI treatment can be improved.

Although the first embodiment is explained in the case where a plaque-depth information image is displayed by superimposing over an X-ray image, if a blood vessel to be imaged has a complex shape, an X-ray image may be sometimes difficult to see caused by a plaque-depth information image in some cases. A second embodiment according to the present invention is explained below in a case where an image that plaque-depth information is superimposed on a Maximum Intensity Projection (MIP) image of three-dimensional volume data is created, and the created image is displayed in parallel at a position at which visibility of an X-ray image is not disturbed.

Figure 8:
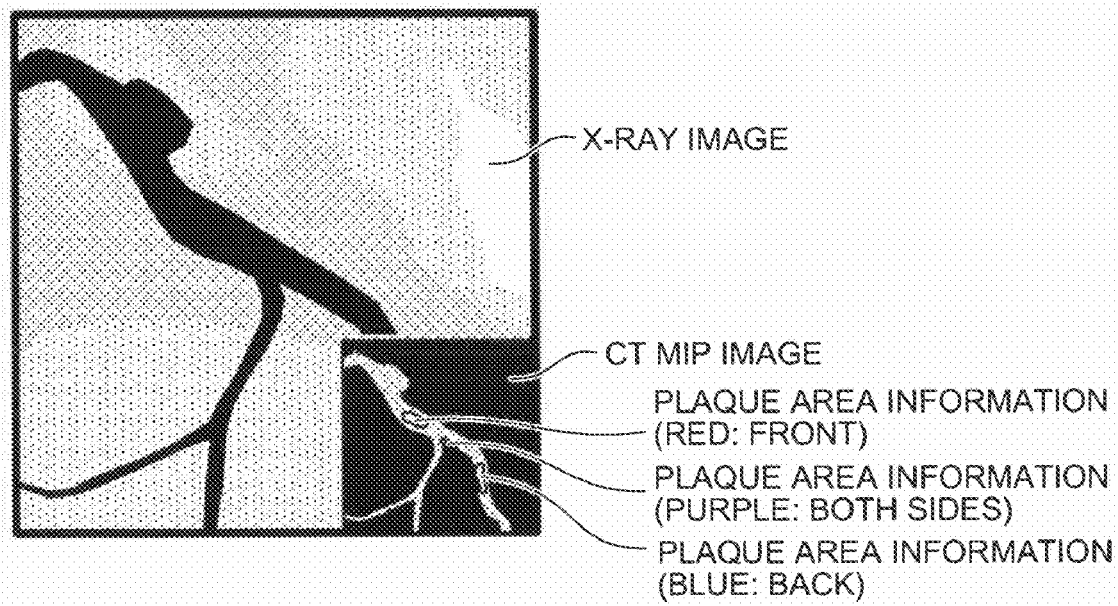
FIG. 8 is a schematic diagram for explaining a concept of depth information display performed by an X-ray angiographic apparatus according to a second embodiment of the present invention.

First of all, a concept of depth information display performed by an X-ray angiographic apparatus according to the second embodiment is explained below. FIG. 8 is a schematic diagram for explaining a concept of depth information display performed by the X-ray angiographic apparatus according to the second embodiment. Compared with the X-ray angiographic apparatus according to the first embodiment that displays a plaque-depth information image over an X-ray image in a superimposed manner, the X-ray angiographic apparatus according to the second embodiment creates an image, as shown in the figure, that a plaque-depth information image (plaque-depth information that the plaque is to be displayed in red when it is present in front of the blood-vessel core line, or in blue when present in the back, or in purple when present on the both sides) is superimposed over an MIP image of three-dimensional volume data obtained from a CT image, reduces the created image in size, and displays it at a certain position on an X-ray image.

In this way, the X-ray angiographic apparatus according to the second embodiment has a main feature configured to display during a PCI treatment on an X-ray image in parallel, an image that an image of plaque area information of which display pattern (color, in this case) is changed in accordance with whether the plaque is present in front of or in the back of a blood-vessel core line, is superimposed on an MIP image. According to the feature, the X-ray angiographic apparatus according to the second embodiment is configured to display information about depth without disturbing visibility of the X-ray image, and to enable an operator to moves a guide wire forward inside a blood vessel without damaging a plaque.

A configuration of the X-ray angiographic apparatus according to the second embodiment is explained below. The configuration of the X-ray angiographic apparatus according to the second embodiment is basically the same as the configuration shown in FIG. 2, and only details of the image processing unit are different. Therefore, a configuration and a processing procedure of an image processing unit according to the second embodiment are explained below. For convenience of explanation, functional units that play roles similar to those of the units shown in FIG. 3 are assigned with the same reference numerals, and detailed explanations of them are omitted.

Figure 9:
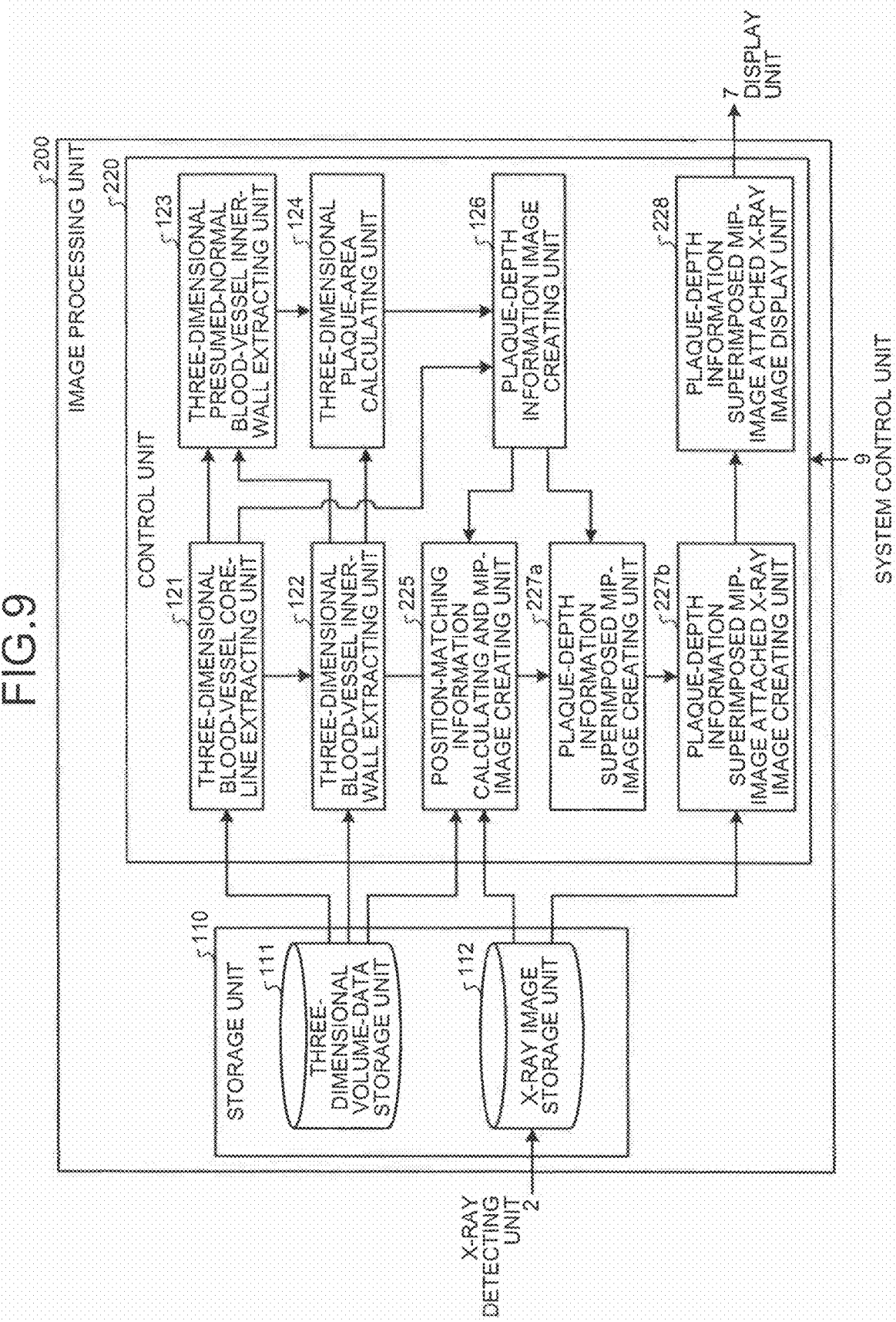
FIG. 9 is a functional block diagram of a configuration of an image processing unit according to the second embodiment.

FIG. 9 is a functional block diagram of a configuration of an image processing unit 200 according to the second embodiment. As shown in the figure, the image processing unit 200 includes the storage unit 110 and a control unit 220.

The control unit 220 controls processing of X-ray image data received from the X-ray detecting unit 2, under the control of the system control unit 9. As units relevant to the present invention, the control unit 220 includes, the three-dimensional blood-vessel core-line extracting unit 121, the three-dimensional blood-vessel inner-wall extracting unit 122, the three-dimensional presumed normal-blood-vessel inner-wall extracting unit 123, the three-dimensional plaque-area calculating unit 124, a position-matching information calculating and MIP-image creating unit 225, the plaque-depth information image creating unit 126, and a plaque-depth information superimposed MIP-image creating unit 227a, a plaque-depth information superimposed MIP-image attached X-ray image creating unit 227b, and a plaque-depth information superimposed MIP-image attached X-ray image display unit 228.

The position-matching information calculating and MIP-image creating unit 225 acquires position-matching parameters from three-dimensional volume data stored in the three-dimensional volume-data storage unit 111, namely, the projection direction, the position, and the magnification, which are parameters to be required for creating an image having the same projection direction, position, and magnification as those of an X-ray image stored in the X-ray image storage unit 112; and furthermore, creates an MIP image based on the acquired positional parameters.

For example, the position-matching information calculating and MIP-image creating unit 225 creates an MIP image by acquiring position-matching parameters according to the method similar to that of the position-matching information calculating unit 125 as explained in the first embodiment.

The plaque-depth information superimposed MIP-image creating unit 227a creates a two-dimensional image that the plaque-depth information image created by the plaque-depth information image creating unit 126 is superimposed over the MIP image created by the position-matching information calculating and MIP-image creating unit 225 (hereinafter, "plaque-depth information superimposed MIP-image").

The plaque-depth information superimposed MIP-image attached X-ray image creating unit 227b acquires an X-ray image stored in the X-ray image storage unit 112, and creates at a certain position on the X-ray image (for example, lower right) a two-dimensional image that is reduced in size from the plaque-depth information superimposed MIP-image created by the plaque-depth information superimposed MIP-image creating unit 227a and superimposed (hereinafter, "plaque-depth information superimposed MIP-image attached X-ray image").

The plaque-depth information superimposed MIP-image attached X-ray image display unit 228 displays the plaque-depth information superimposed MIP-image attached X-ray image created by the plaque-depth information superimposed MIP-image attached X-ray image creating unit 227b onto the display unit 7.

Figure 10:
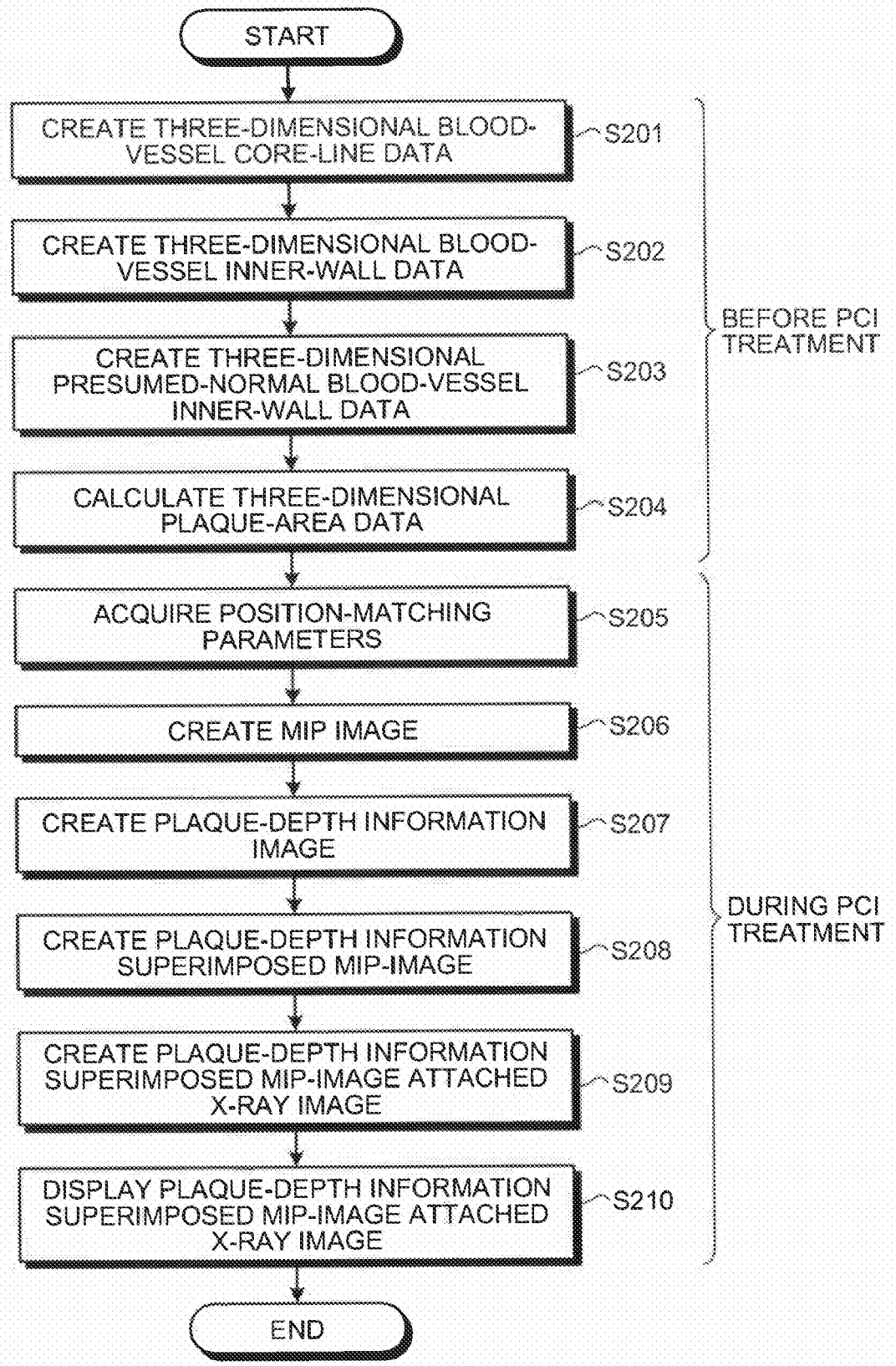
FIG. 10 is a flowchart of a processing procedure of the image processing unit according to the second embodiment.

A processing procedure of the image processing unit 200 according to the second embodiment is explained below. FIG. 10 is a flowchart of the processing procedure of the image processing unit 200 according to the second embodiment. As shown in the figure, to begin with, the image processing unit 200 performs the processing similar to Steps S101 to S104 shown in FIG. 7 prior to a PCI treatment (Step S201 to S204).

During the PCI treatment, the position-matching information calculating and MIP-image creating unit 225 acquires position-matching parameters from three-dimensional volume data stored in the three-dimensional volume-data storage unit 111, namely, a projection direction, a position, and a magnification, which are parameters to be required for creating an image having the same projection direction, position, and magnification as those of an X-ray image stored in the X-ray image storage unit 112 (Step S205), and furthermore, creates an MIP image based on the acquired positional parameters (Step S206).

Subsequently, the plaque-depth information image creating unit 126 creates a plaque-depth information image based on the three-dimensional blood-vessel core-line data created by the three-dimensional blood-vessel core-line extracting unit 121, the three-dimensional plaque-area data calculated by the three-dimensional plaque-area calculating unit 124, and the position-matching parameters acquired by the position-matching information calculating and MIP-image creating unit 225 (Step S207).

Subsequently, the plaque-depth information superimposed MIP-image creating unit 227a creates a plaque-depth information superimposed MIP-image that the plaque-depth information image created by the plaque-depth information image creating unit 126 is superimposed over the MIP image created by the position-matching information calculating and MIP-image creating unit 225 (Step S208).

After that, the plaque-depth information superimposed MIP-image attached X-ray image creating unit 227b acquires an X-ray image stored in the X-ray image storage unit 112, and creates at a certain position on the X-ray image a plaque-depth information superimposed MIP-image attached X-ray image that is reduced in size from the plaque-depth information superimposed MIP-image created by the plaque-depth information superimposed MIP-image creating unit 227a and superimposed (Step S209).

The plaque-depth information superimposed MIP-image attached X-ray image display unit 228 then displays the plaque-depth information superimposed MIP-image attached X-ray image created by the plaque-depth information superimposed MIP-image attached X-ray image creating unit 227b onto the display unit 7 (Step S210).

As described above, according to the second embodiment, during a PCI treatment, the position-matching information calculating and MIP-image creating unit 225 acquires position-matching parameters, namely, the projection direction, the position, and the magnification, and furthermore, creates an MIP image based on the acquired position-matching parameters. Subsequently, the plaque-depth information superimposed MIP-image creating unit 227a creates a plaque-depth information superimposed MIP-image that the plaque-depth information image created by the plaque-depth information image creating unit 126 is superimposed over the MIP image created by the position-matching information calculating and MIP-image creating unit 225.

Further subsequently, the plaque-depth information superimposed MIP-image attached X-ray image creating unit 227b creates at a certain position on the X-ray image a plaque-depth information superimposed MIP-image attached X-ray image that is reduced in size from the plaque-depth information superimposed MIP-image. The plaque-depth information superimposed MIP-image attached X-ray image display unit 228 then displays the plaque-depth information superimposed MIP-image attached X-ray image onto the display unit 7.

Thus, according to the above configuration, the second embodiment is configured such that by displaying information about a depth without disturbing visibility of an X-ray image, when an operator moves a guide wire forward inside a blood vessel, the operator can easily determine an appropriate turning direction of the guide wire. Moreover, the X-ray angiographic apparatus can assist the operator to move the guide wire forward inside a blood vessel without damaging a plaque.

Although the first and second embodiments are configured such that a plaque area present in front of the blood-vessel core line and a plaque area present in the back are differently displayed by changing the color, the present invention is not limited to this, and it can be configured to change a graphical pattern.

Although the first and second embodiments are explained in the case where the X-ray angiographic apparatus displays information that represents a position in depth of a blood-vessel lesion-site (a plaque), a third embodiment according to the present invention is explained below in a case where the X-ray angiographic apparatus displays information that represents a running direction of a blood vessel.

First of all, a concept of displaying blood-vessel running-direction information performed by an X-ray angiographic apparatus according to the third embodiment is explained below. The X-ray angiographic apparatus according to the third embodiment creates, prior to a PCI treatment, a three-dimensional blood-vessel core line that represents a core line of a blood vessel to be imaged based on three-dimensional volume data (three-dimensional image data) obtained from a CT image imaged in advance by an X-ray CT apparatus. During the PCI treatment, the X-ray angiographic apparatus then creates a blood-vessel running-direction information image on which a blood vessel is displayed with variations to indicate a running direction of the blood vessel based on positional information in relation to the three-dimensional blood-vessel core line created before the treatment.

Figure 11:
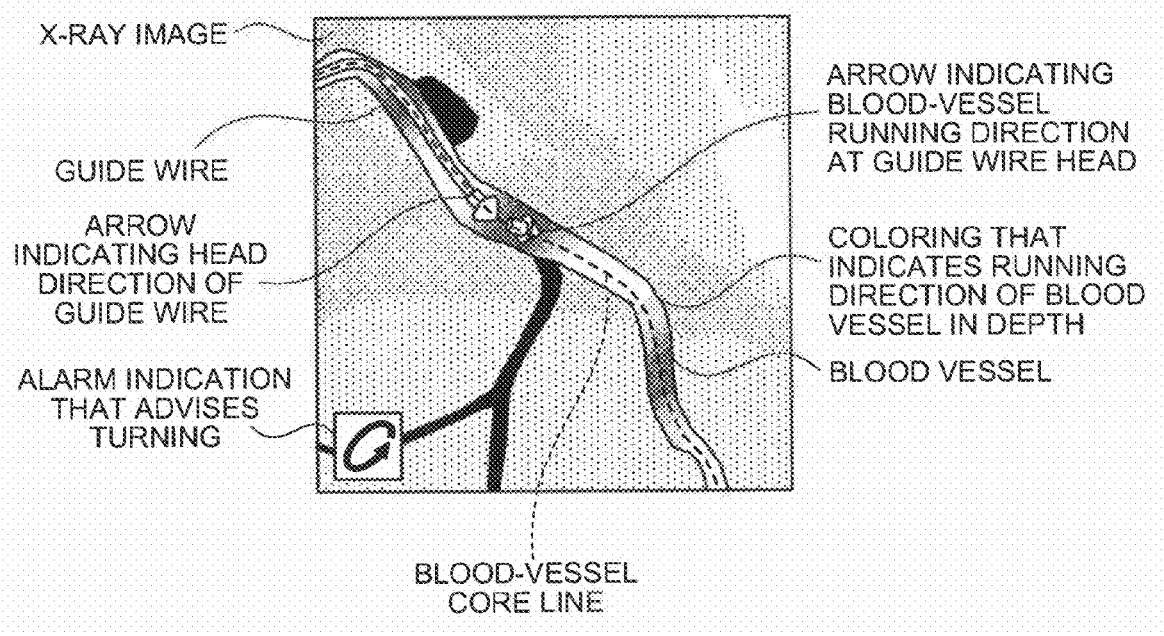
FIG. 11 is a schematic diagram for explaining a concept of blood-vessel running-direction information display performed by an X-ray angiographic apparatus according to a third embodiment of the present invention.

FIG. 11 is a schematic diagram for explaining a concept of displaying blood-vessel running-direction information performed by the X-ray angiographic apparatus according to the third embodiment. As shown in the figure, for example, the X-ray angiographic apparatus creates a blood-vessel running-direction information image in which the color of a blood vessel is varied in accordance with whether the blood vessel is shallow or deep in the projection direction. The X-ray angiographic apparatus then displays the created blood-vessel running-direction information image over an X-ray image in a superimposed manner, as shown in the figure.

Thus, because the X-ray angiographic apparatus according to the third embodiment displays an image of a blood vessel of which color is varied in accordance with whether the blood vessel is shallow or deep in the projection direction, an operator can easily grasp a blood-vessel running direction. In other words, the X-ray angiographic apparatus according to the third embodiment is configured to provide information indicating a blood-vessel running direction, and to enable an operator to determine an appropriate turning direction of a guide wire easily.

As shown in the figure, the X-ray angiographic apparatus according to the third embodiment further displays a graphic image (a three-dimensional arrow) that indicates a head direction of the guide wire, and a graphic image (a three-dimensional arrow) that indicates a blood-vessel running direction at the head position of the guide wire. Moreover, if a relative angle between the head direction of the guide wire and the blood-vessel running direction at the guide-wire head position exceeds a predetermined threshold value, the X-ray angiographic apparatus according to the third embodiment displays on the X-ray image additionally an alarm indication that advises turning the guide wire.

A configuration of the X-ray angiographic apparatus according to the third embodiment is explained below. The configuration of the X-ray angiographic apparatus according to the third embodiment is basically the same as the configuration shown in FIG. 2, and only details of the image processing unit are different. Therefore, a configuration and a processing procedure of an image processing unit according to the third embodiment are explained below.

Figure 12:
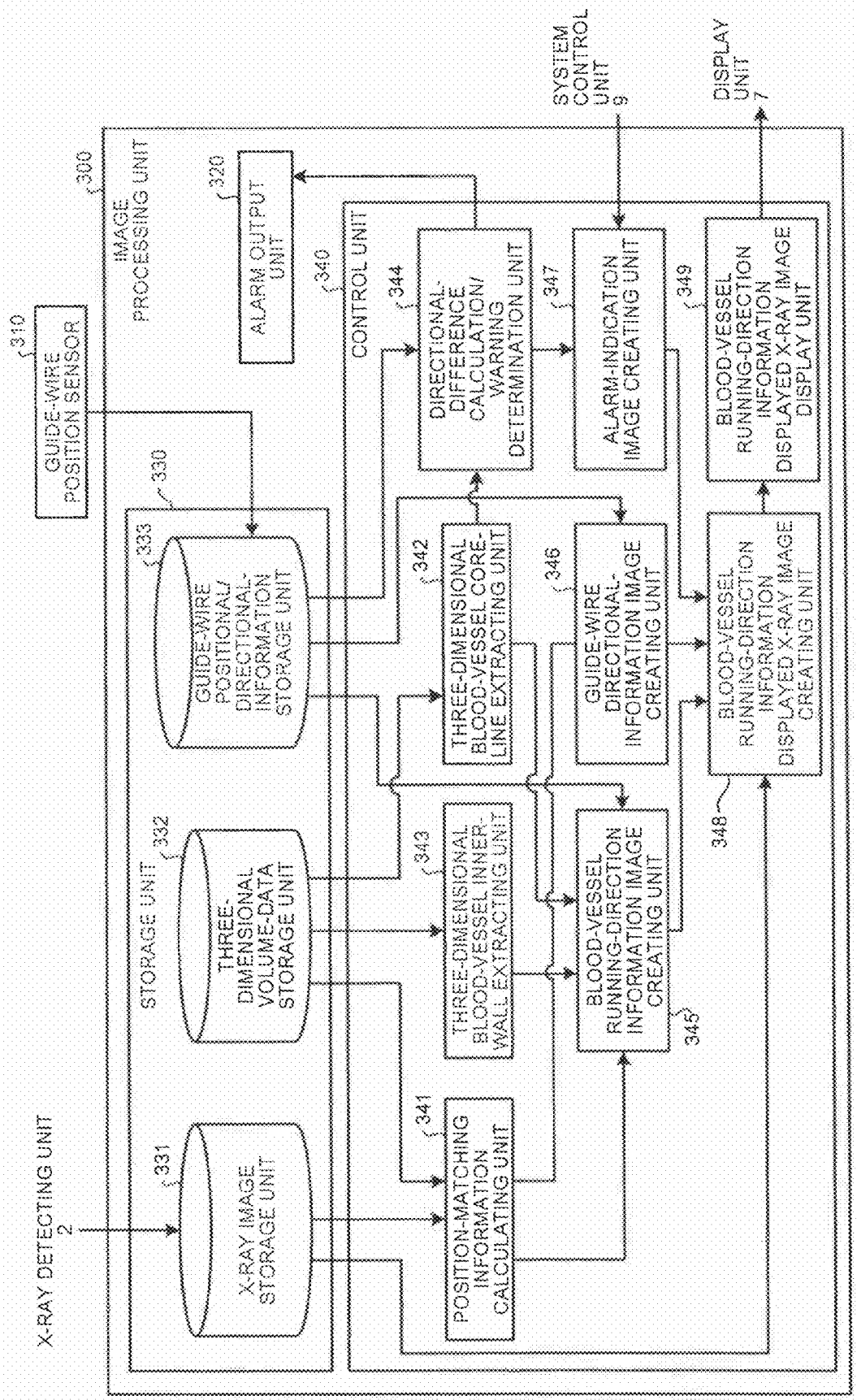
FIG. 12 is a functional block diagram of a configuration of an image processing unit according to the third embodiment.

FIG. 12 is a functional block diagram of a configuration of an image processing unit 300 according to the third embodiment. As shown in the figure, the image processing unit 300 includes a guide-wire position sensor 310, an alarm output unit 320, a storage unit 330, and a control unit 340.

The guide-wire position sensor 310 is a position sensor mounted on the head of the guide wire, and detects the head position and the head direction of the guide wire.

The alarm output unit 320 is a device that outputs an alarm when a relative angle between the head direction of the guide wire and the blood-vessel running direction at the guide-wire head position exceeds a predetermined threshold value.

The storage unit 330 stores therein data and a program required for the control unit 340 to perform various processing. The storage unit 330 includes an X-ray image storage unit 331, a three-dimensional volume-data storage unit 332, and a guide-wire positional/directional-information storage unit 333.

The X-ray image storage unit 331 stores therein X-ray images of a heart area imaged by the X-ray angiographic apparatus. The X-ray image storage unit 331 stores therein X-ray images collected in real time with regular intervals during a PCI treatment. If an X-ray image is imaged by I. I., a deformation of an image of I. I. needs to be corrected in real time.

The three-dimensional volume-data storage unit 332 stores therein three-dimensional volume data of an image of the heart area imaged by performing coronary imaging with an X-ray CT apparatus. The three-dimensional volume-data storage unit 332 stores therein prior to a PCI treatment three-dimensional volume data of an image imaged in advance by the X-ray CT apparatus.

The guide-wire positional/directional-information storage unit 333 stores therein information that indicates the head position and the head direction of the guide wire detected by the guide-wire position sensor 310. The stored information that indicates the head position and the head direction is converted onto a coordinate system of the three-dimensional volume data acquired from the three-dimensional volume-data storage unit 332.

The control unit 340 controls processing of X-ray image data received from the X-ray detecting unit 2, under the control of the system control unit 9. The control unit 340 includes a position-matching information calculating unit 341, a three-dimensional blood-vessel core-line extracting unit 342, a three-dimensional blood-vessel inner-wall extracting unit 343, a directional-difference calculation/warning determination unit 344, a blood-vessel running-direction information image creating unit 345, a guide-wire directional-information image creating unit 346, an alarm-indication image creating unit 347, a blood-vessel running-direction information displayed X-ray image creating unit 348, and a blood-vessel running-direction information displayed X-ray image display unit 349.

The position-matching information calculating unit 341 acquires position-matching parameters from three-dimensional volume data stored in the three-dimensional volume-data storage unit 332, namely, the projection direction, the position, and the magnification, which are to be required for creating an image of the same projection direction, position, and magnification as those of the X-ray image stored in the X-ray image storage unit 331.

It is assumed that the position-matching information calculating unit 341 acquires position-matching parameters from the system control unit 9. It is assumed that a coordinate system that is a reference of the acquired projection direction, position, and magnification is equal to a coordinate system that is a reference of parameters acquired as additional information of an X-ray CT image, or can be converted one-to-one.

The three-dimensional blood-vessel core-line extracting unit 342 creates data that represents a core line of a coronary artery on which the PCI treatment is to be performed (hereinafter, "three-dimensional blood-vessel core-line data") based on CT values of three-dimensional volume data stored in the three-dimensional volume-data storage unit 332.

Specifically, the three-dimensional blood-vessel core-line extracting unit 342 creates three-dimensional blood-vessel core-line data as three-dimensional point-series data. As a data structure and a creation algorithm to create such three-dimensional blood-vessel core-line data, a data structure and a creation algorithm according to a known technology, such as the technology described in JP-A 2004-283373 (KOKAI), are used.

The three-dimensional blood-vessel inner-wall extracting unit 343 creates data that represents a blood-vessel inner wall around the blood-vessel core line (hereinafter, "three-dimensional blood-vessel inner-wall data"), based on the CT values of the three-dimensional volume data stored in the three-dimensional volume-data storage unit 332, and the three-dimensional blood-vessel core line created by the three-dimensional blood-vessel core-line extracting unit 342.

Specifically, the three-dimensional blood-vessel inner-wall extracting unit 343 creates three-dimensional blood-vessel inner-wall data as three-dimensional point-series data. As a data structure and a creation algorithm to create such three-dimensional blood-vessel inner-wall data, a data structure and a creation algorithm according to a known technology, such as the technology described in JP-A 2004-283373 (KOKAI), are used.

The directional-difference calculation/warning determination unit 344 determines whether a relative angle between the head direction of the guide wire and the blood-vessel running direction at the guide-wire head position exceeds a predetermined threshold value. Specifically, the directional-difference calculation/warning determination unit 344 calculates a relative angle between the head direction of the guide wire and the blood-vessel running direction at the guide-wire head position based on the three-dimensional blood-vessel core-line data created by the three-dimensional blood-vessel core-line extracting unit 342, and the head position and the head direction of the guide wire detected by the guide-wire position sensor 310.

The directional-difference calculation/warning determination unit 344 then determines whether the calculated relative angle exceeds a predetermined threshold value (for example, 45 degrees), and if it is determined that the angle exceeds the threshold value, the directional-difference calculation/warning determination unit 344 controls the alarm output unit 320 and makes the alarm output unit 320 output an alarm.

Figure 13:
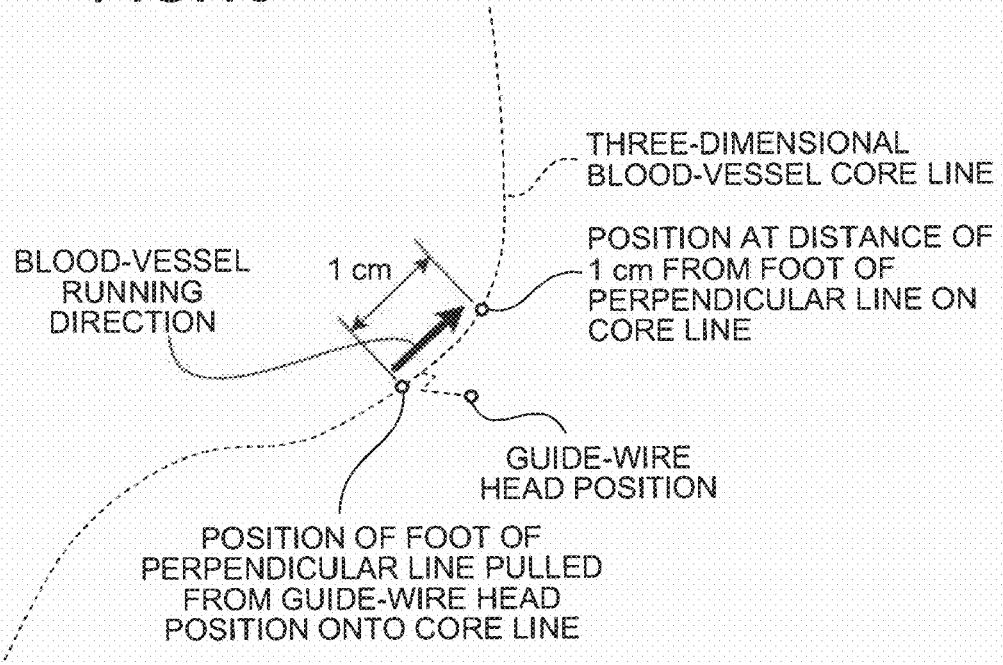
FIG. 13 is a schematic diagram for explaining an example of a method of calculating a blood-vessel running direction at a head position of a guide wire.

An example of a method of calculating a blood-vessel running direction at the head position of the guide wire is explained below. FIG. 13 is a schematic diagram for explaining an example of a method of calculating a blood-vessel running direction at the head position of the guide wire. As shown in the figure, for example, where a perpendicular line is pulled down from the head position of the guide wire to the three-dimensional blood-vessel core line, the directional-difference calculation/warning determination unit 344 calculates, as a blood-vessel running direction, the direction of a vector defined by a line connecting the position of an intersection of the perpendicular line and the three-dimensional blood-vessel core line to a position at a predetermined distance (for example, one centimeter ahead) from the intersection.

The blood-vessel running-direction information image creating unit 345 creates a blood-vessel running-direction information image on which the blood vessel is displayed in variation to indicate the blood-vessel running direction, based on the three-dimensional blood-vessel core-line data created by the three-dimensional blood-vessel core-line extracting unit 342, the three-dimensional blood-vessel inner-wall data created by the three-dimensional blood-vessel inner-wall extracting unit 343, and the position-matching parameters (projection direction, position, and magnification) acquired by the position-matching information calculating unit 341.

Specifically, when projecting the three-dimensional blood-vessel core line based on the position-matching parameters obtained by the position-matching information calculating unit 341, the blood-vessel running-direction information image creating unit 345 creates a two-dimensional graphic image as a blood-vessel running-direction information image, on which a two-dimensional blood-vessel core line and a two-dimensional blood-vessel area (an area enclosed by an blood-vessel inner wall obtained by projecting the three-dimensional blood-vessel inner-wall data) are colored in accordance with a position of each point on the three-dimensional blood-vessel core line, and the other areas are colorless.

The two-dimensional graphic image created as a blood-vessel running-direction information image is a 32-bit color RGBA image of which color is expressed in a combination of an R value (red), a G value (green), a B value (blue), and an A value (transparency). The blood-vessel running-direction information image creating unit 345 takes the A value of 128 (translucent) for pixels on the two-dimensional blood-vessel core line and in the two-dimensional blood-vessel area, and takes the A value of zero (transparent) for pixels in the other areas, on the blood-vessel running-direction information image.

Moreover, the blood-vessel running-direction information image creating unit 345 performs coloring processing of the two-dimensional blood-vessel core line and the two-dimensional blood-vessel area both of which are projected on the blood-vessel running-direction information image by setting RGB values of pixels corresponding to respective points in accordance with a position of each of the points on the three-dimensional blood-vessel core line. As a method of coloring processing, for example, there are three methods as described below. Although the following description explains coloring of a two-dimensional blood-vessel core line, the blood-vessel running-direction information image creating unit 345 according to the third embodiment also colors a two-dimensional blood-vessel area that is an area enclosed by a blood-vessel inner wall obtained by projecting three-dimensional blood-vessel inner-wall data similarly to coloring of a two-dimensional blood-vessel core line.

(A) Coloring Processing Based on Relative Distance

For example, the blood-vessel running-direction information image creating unit 345 changes RGB values of the two-dimensional blood-vessel core line on the blood-vessel running-direction information image in accordance with a position of a three-dimensional blood-vessel core line along the projection direction. In such case, specifically, the blood-vessel running-direction information image creating unit 345 creates an image with pixels in front of the three-dimensional blood-vessel core line in the projection direction in red, and pixels in the back in blue.

Figure 14:
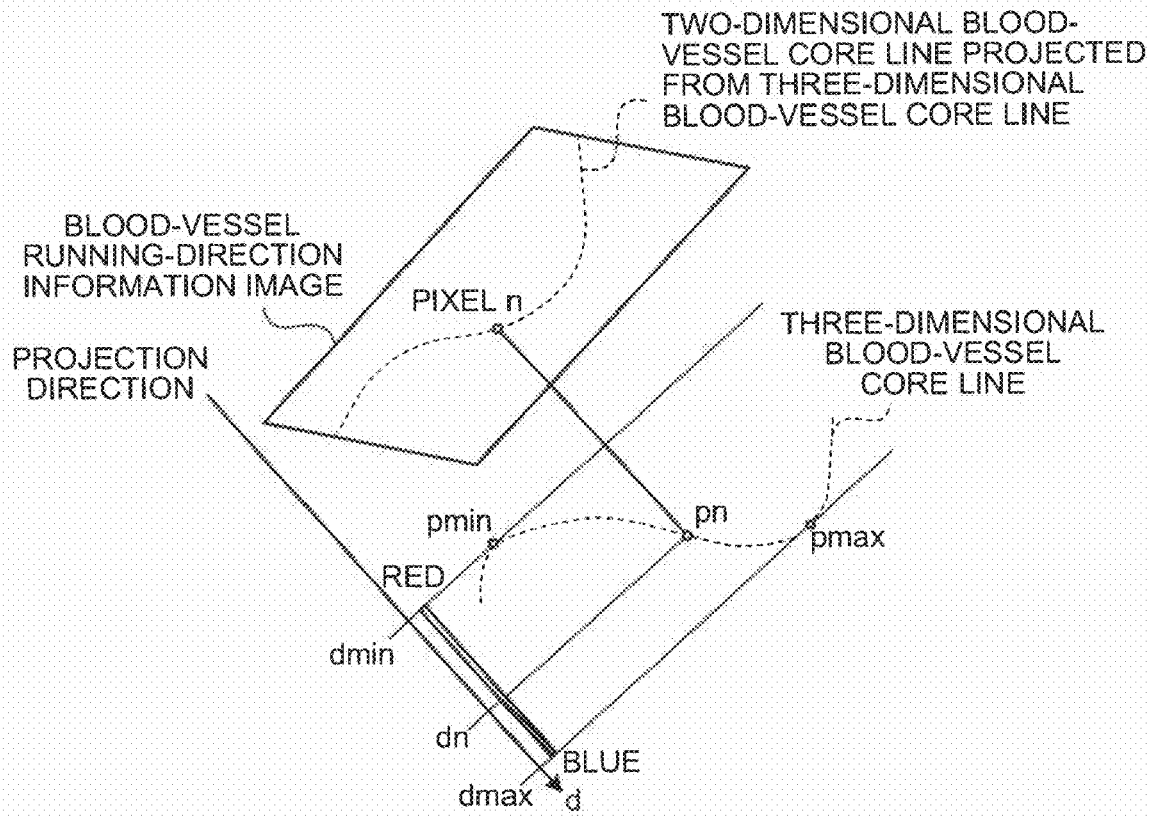
FIG. 14 is a schematic diagram for explaining coloring processing to be performed on a two-dimensional blood-vessel core line based on a relative distance.

FIG. 14 is a schematic diagram for explaining coloring processing to be performed on a two-dimensional blood-vessel core line based on a relative distance. As shown in the figure, for example, suppose a pixel on the two-dimensional blood-vessel core line on a blood-vessel running-direction information image is n, a point on the three-dimensional blood-vessel core line corresponding to the pixel n is pn, a point present at the most front in the projection direction is pmin, a point present at the most back in the projection direction is pmax, a distance to the point pn in the projection direction is dn, a distance to the point pmin is dmin, and a distance to the point pmax is dmax. The blood-vessel running-direction information image creating unit 345 determines RGB values of the pixel n on the two-dimensional blood-vessel core line in the blood-vessel running-direction information image based on Expression (1) as follows:

$$(R,G,B)=(255\times(d\mathrm{max}-dn)/(d\mathrm{max}-d\mathrm{min}),0,255\times(dn-d\mathrm{min})/(d\mathrm{max}-d\mathrm{min})) \quad (1)$$

It can be configured such that a user can set arbitrary values of the variables dmin and dmax among the above variables.

(B) Coloring Processing Based on Inclination

Alternatively, for example, the blood-vessel running-direction information image creating unit 345 changes RGB values of the two-dimensional blood-vessel core line on the blood-vessel running-direction information image in accordance with an inclination of the three-dimensional blood-vessel core line with respect to the projection direction. In such case, specifically, the blood-vessel running-direction information image creating unit 345 creates an image with pixels on a portion of the blood vessel in a blood-vessel running direction rather similar to the projection direction (deep in the screen) in blue, and pixels on a portion of the blood vessel in the reverse direction of the projection direction (shallow in the screen) in red.

Figure 15:
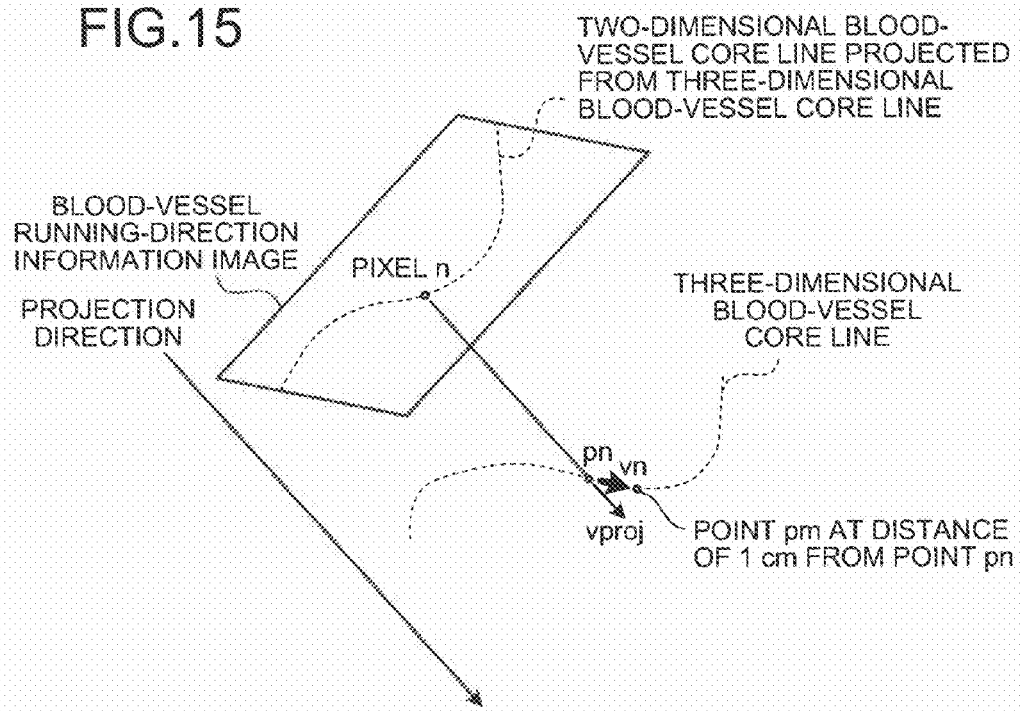
FIG. 15 is a schematic diagram for explaining coloring processing to be performed on a two-dimensional blood-vessel core line based on an inclination.

FIG. 15 is a schematic diagram for explaining coloring processing to be performed on a two-dimensional blood-vessel core line based on an inclination. As shown in the figure, for example, suppose a point at a predetermined distance (for example, one centimeter) from the point pn corresponding the pixel n is pm, a unit vector defined by a line connecting between the point pn and the point pm is vn, and a unit vector in the projection direction is vproj. The blood-vessel running-direction information image creating unit 345 determines RGB values of the pixel n on the two-dimensional blood-vessel core line on the blood-vessel running-direction information image based on Expression (2) as follows:

$$(R,G,B)=(255\times(1-vn\cdot v\mathrm{proj})/2,0,255\times(vn\cdot v\mathrm{proj}+1)/2) \quad (2)$$

where vn·vproj denotes an inner product of the vector vn and the vector vproj in Expression (2).

(C) Coloring Processing Based on Curvature Ratio

Alternatively, for example, the blood-vessel running-direction information image creating unit 345 changes RGB values of the two-dimensional blood-vessel core line on the blood-vessel running-direction information image in accordance with a curvature ratio of the three-dimensional blood-vessel core line. In such case, specifically, the blood-vessel running-direction information image creating unit 345 creates an image in red where a curvature ratio of a running blood vessel is large, and in blue where the curvature read is small.

Figure 16:
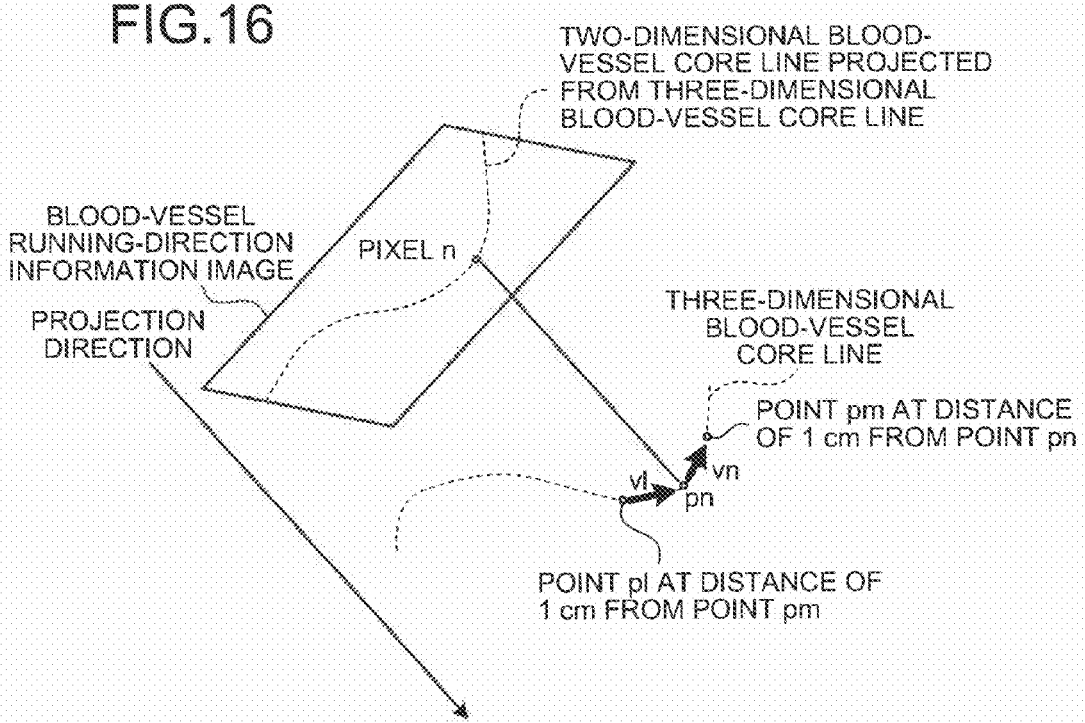
FIG. 16 is a schematic diagram for explaining coloring processing to be performed on a two-dimensional blood-vessel core line based on a curvature ratio.

FIG. 16 is a schematic diagram for explaining coloring processing to be performed on a two-dimensional blood-vessel core line based on a curvature ratio. As shown in the figure, for example, suppose a point at a predetermined distance (for example, one centimeter) from the point pn on the three-dimensional blood-vessel core line corresponding the pixel n is pl, a point at a predetermined distance from the point pn in the reverse direction is pm, a unit vector defined by a line connecting between the point pn and the point pl is vl, and a unit vector defined by a line connecting between the point pn and the point pm is vn. The blood-vessel running-direction information image creating unit 345 determines RGB values of the pixel n on the two-dimensional blood-vessel core line on the blood-vessel running-direction information image based on Expression (3) as follows:

$$(R,G,B)=(255\times(1-vl\cdot vn)/2, 0, 255\times(vl\cdot vn+1)/2) \quad (3)$$

where vl·vn denotes an inner product of the vector vl and the vector vn in Expression (3).

Although according to the above methods, colors corresponding to the lower limit and the upper limit are red and blue, respectively, a user can arbitrarily set colors (RGB values) of the lower limit and the upper limit, and the transparency (A value).

It is desirable that selection of a method from among the above three method to display a two-dimensional blood-vessel core line on a blood-vessel running-direction information image can be determined so as to display blood-vessel running-direction information by switching among the methods or to display different information simultaneously, in accordance with an instruction from a user. As a method of displaying different blood-vessel running-direction information simultaneously, for example, a method is conceivable such that after coloring the two-dimensional blood-vessel core line based on the method (A), the vectors used in the methods (B) and (C) are indicated as an angle of a three-dimensional arrow.

Furthermore, the blood-vessel running-direction information image creating unit 345 calculates a blood-vessel running direction at the guide-wire head position by using three-dimensional blood-vessel core-line data created by the three-dimensional blood-vessel core-line extracting unit 342, and information about the head position and the head direction of the guide wire stored in the guide-wire positional/directional-information storage unit 333.

A method of calculating a blood-vessel running direction at the guide-wire head position is the same method as explained above with reference to FIG. 13. The blood-vessel running-direction information image creating unit 345 then creates an image indicating the calculated blood-vessel running direction, and superimposes the created image over the blood-vessel running-direction information image explained above.

Figure 17A:
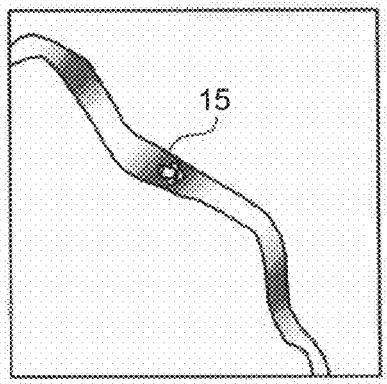
FIGS. 17A to 17D are schematic diagrams illustrating intermediate images created by the image processing unit according to the third embodiment.

FIGS. 17A to 17D are schematic diagrams illustrating intermediate images created by the image processing unit 300 according to the third embodiment. For example, as shown in FIG. 17A, the blood-vessel running-direction information image creating unit 345 indicates a blood-vessel running direction at the guide-wire head position with a graphic image 15 that is a three-dimensional arrow projected in accordance with the position-matching parameters (projection direction, position, and magnification) obtained by the position-matching information calculating unit 341, and superimposes the graphic image 15 over the blood-vessel running-direction information image.

Additionally, for example, as described in the technology described in JP-A 2004-283373 (KOKAI), depth information about a coarctation area inside the blood vessel can be displayed in a superimposed manner over an X-ray image by using a technology of extracting a blood-vessel core line, a blood-vessel inner wall, and a presumed-normal blood-vessel inner wall from three-dimensional volume data. In such case, for example, as depth information, a graphic image that represents a lesion-site, such as a plaque, can be displayed in a superimposed manner over an X-ray image by changing the color in accordance with whether the lesion-site is present in front of or in the back of the blood-vessel core line.

In this way, when displaying depth information about an coarctation area of a blood vessel by coloring additionally to the colored display of a blood-vessel running direction as explained above, information can be displayed in a superimposed manner as rendered in different color arrangement of the color scale (for example, blood-vessel running-direction information is to be rendered in red to blue, and coarctation-area depth information is to be rendered in yellow to green).

The guide-wire directional-information image creating unit 346 creates an image that represents the head direction of a guide wire inserted in a blood vessel (hereinafter, "guide-wire directional-information image") based on the head position and the head direction of the guide wire detected by the guide-wire position sensor 310.

Figure 17B:
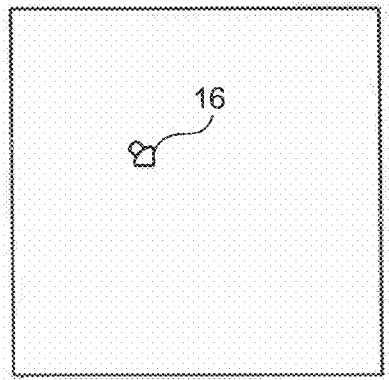

For example, as shown in FIG. 17B, the guide-wire directional-information image creating unit 346 creates, as a guide-wire directional-information image, a graphic image 16 represented by a three-dimensional arrow that is projected in accordance with the position-matching parameters (projection direction, position, and magnification) obtained by the position-matching information calculating unit 341.

The alarm-indication image creating unit 347 creates an alarm indication image that warns that the moving direction of the guide wire is different from the blood-vessel running direction, when the directional-difference calculation/warning determination unit 344 determines that a relative angle between the head direction of the guide wire and the blood-vessel running direction at the guide-wire head position exceeds a predetermined threshold value.

Figure 17C:
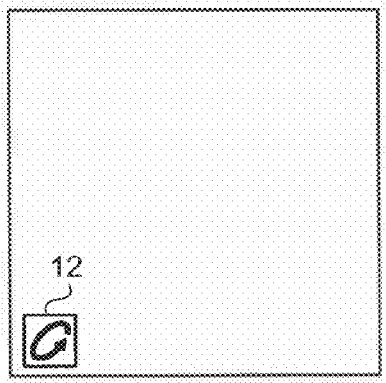

For example, as shown in FIG. 17C, the alarm-indication image creating unit 347 creates an image that contains an alarm indication 12 for advising turning the guide wire.

The blood-vessel running-direction information displayed X-ray image creating unit 348 acquires an X-ray image stored in the X-ray image storage unit 331, and creates, as a blood-vessel running-direction information displayed X-ray image, a two-dimensional image that the blood-vessel running-direction information image created by the blood-vessel running-direction information image creating unit 345, the guide-wire directional-information image created by the guide-wire directional-information image creating unit 346, and the alarm indication image created by the alarm-indication image creating unit 347 are superimposed over the acquired X-ray image.

Figure 17D:
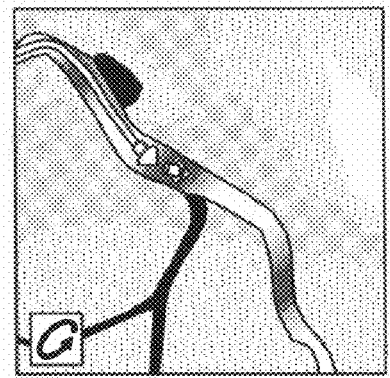

For example, the blood-vessel running-direction information displayed X-ray image creating unit 348 creates a blood-vessel running-direction information displayed X-ray image as shown in FIG. 17D by superimposing the images shown in FIGS. 17A to 17C over the X-ray image. When creating such blood-vessel running-direction information displayed X-ray image, the blood-vessel running-direction information displayed X-ray image creating unit 348 converts the X-ray image that is the 8-bit into the 24-bit color (RGB) image to synthesize the blood-vessel running-direction information image, the guide-wire directional-information image, and the alarm indication image, each of which is a 32-bit color image.

The blood-vessel running-direction information displayed X-ray image display unit 349 displays the blood-vessel running-direction information displayed X-ray image created by the blood-vessel running-direction information displayed X-ray image creating unit 348 onto the display unit 7.

Although it is explained above in the case where the running direction of a blood vessel at the guide-wire head position is displayed by superimposing the blood-vessel running-direction information displayed X-ray image over the X-ray image, the running direction of the blood vessel can be indicated by using a Virtual Endoscopic (VE) image of three-dimensional volume data as a method of three-dimensionally visualizing the blood-vessel running direction at the guide-wire head position at a branching point of the blood vessel.

Figure 18:
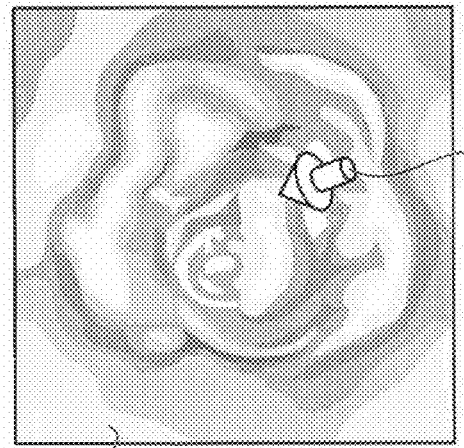
FIG. 18 is a schematic diagram for explaining display of blood-vessel running-direction information when using a Virtual Endoscopic (VE) image.

FIG. 18 is a schematic diagram for explaining display of blood-vessel running-direction information when using a VE image. As shown in the figure, specifically, a three-dimensional graphic image (for example, a three-dimensional arrow) that represents the head position and the head direction of the guide wire is displayed over a VE image of three-dimensional volume data viewed from a position on the blood-vessel core line corresponding to the guide-wire head and the blood-vessel running direction based on information about the head position and the head direction of the guide wire stored in the guide-wire positional/directional-information storage unit 333. Such a VE image is displayed, for example, in parallel with a blood-vessel running-direction information displayed X-ray image.

Figure 19:
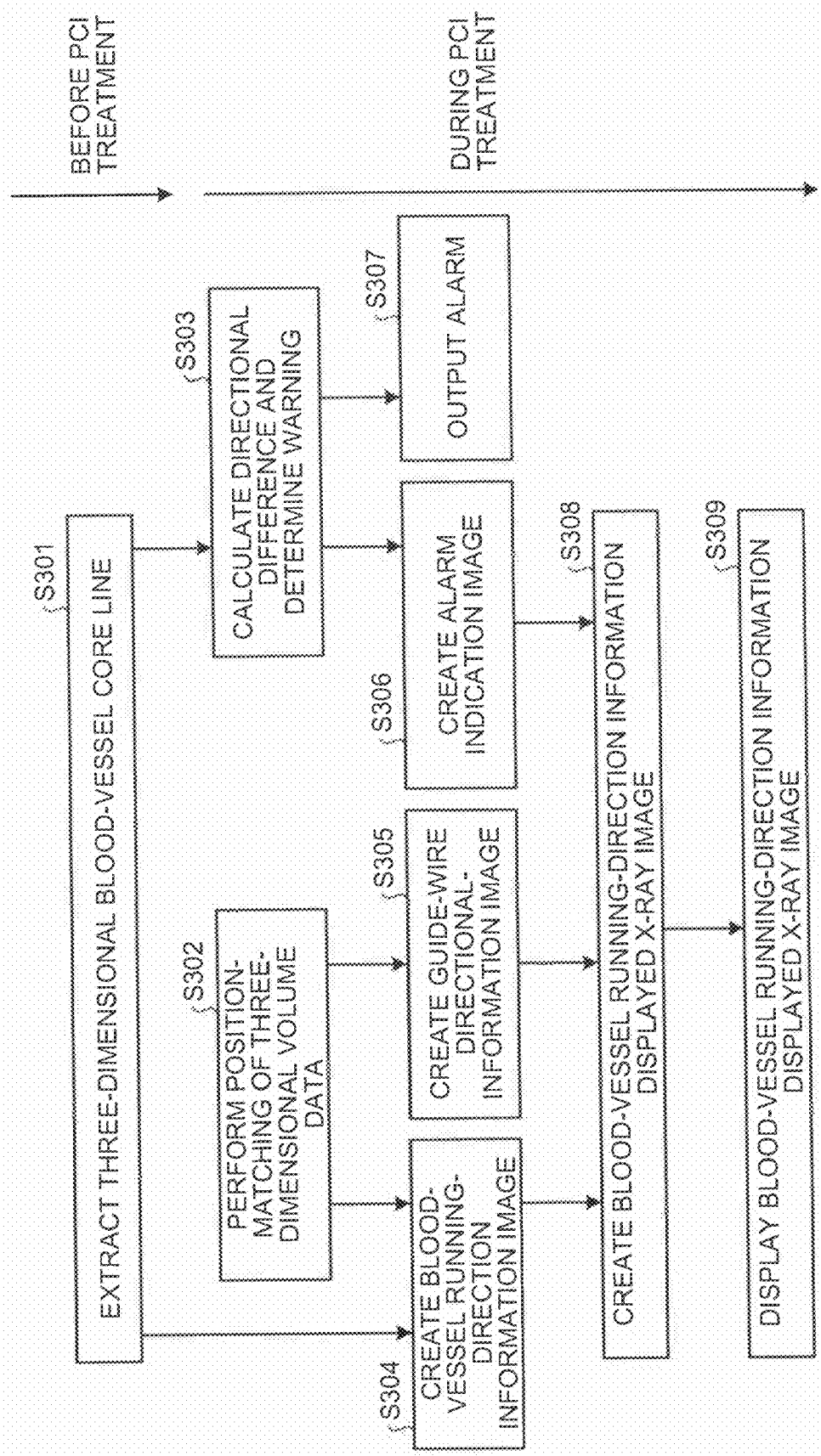
FIG. 19 is a flowchart of a processing procedure of the image processing unit according to the third embodiment.

A processing procedure of the image processing unit 300 according to the third embodiment is explained below. FIG. 19 is a flowchart of the processing procedure of the image processing unit 300 according to the third embodiment. As shown in the figure, according to the image processing unit 300, prior to a PCI treatment, to begin with, the three-dimensional blood-vessel core-line extracting unit 342 creates three-dimensional blood-vessel core-line data of a coronary artery on which the PCI treatment is to be performed based on CT values of three-dimensional volume data stored in the three-dimensional volume-data storage unit 332, and the three-dimensional blood-vessel inner-wall extracting unit 343 creates three-dimensional blood-vessel inner-wall data (Step S301).

During the PCI treatment, the position-matching information calculating unit 341 acquires position-matching parameters from the three-dimensional volume data stored in the three-dimensional volume-data storage unit 332, namely, the projection direction, the position, and the magnification, which are to be required for creating an image of the same projection direction, position, and magnification as those of an X-ray image stored in the X-ray image storage unit 331 (Step S302).

On the other hand, the directional-difference calculation/warning determination unit 344 determines whether a relative angle between the head direction of the guide wire and the blood-vessel running direction at the guide-wire head position exceeds a predetermined threshold value (Step S303).

Subsequently, the blood-vessel running-direction information image creating unit 345 creates a blood-vessel running-direction information image by using the three-dimensional blood-vessel core-line data created by the three-dimensional blood-vessel core-line extracting unit 342, and the position-matching parameters acquired by the position-matching information calculating unit 341 (Step S304).

The guide-wire directional-information image creating unit 346 creates a guide-wire directional-information image that represents the head direction of the guide wire inserted in the blood vessel based on the head position and the head direction of the guide wire detected by the guide-wire position sensor 310 (Step S305).

When the directional-difference calculation/warning determination unit 344 determines that the relative angle between the head direction of the guide wire and the blood-vessel running direction at the guide-wire head position exceeds a predetermined threshold value, the alarm-indication image creating unit 347 creates an alarm indication image that warns that the moving direction of the guide wire is different from the blood-vessel running direction (Step S306), and the alarm output unit 320 outputs an alarm (Step S307).

Subsequently, the blood-vessel running-direction information displayed X-ray image creating unit 348 acquires an X-ray image stored in the X-ray image storage unit 331, and creates a blood-vessel running-direction information displayed X-ray image that the blood-vessel running-direction information image created by the blood-vessel running-direction information image creating unit 345, the guide-wire directional-information image created by the guide-wire directional-information image creating unit 346, and the alarm indication image created by the alarm-indication image creating unit 347 are superimposed over the acquired X-ray image (Step S308).

The blood-vessel running-direction information displayed X-ray image display unit 349 then displays onto the display unit 7 the blood-vessel running-direction information displayed X-ray image created by the blood-vessel running-direction information displayed X-ray image creating unit 348 (Step S309).

As described above, according to the third embodiment, the three-dimensional blood-vessel core-line extracting unit 342 creates, prior to the PCI treatment, a three-dimensional blood-vessel core line that represents the core line of a blood vessel to be imaged based on three-dimensional volume data obtained from an image imaged by an X-ray CT apparatus.

During the PCI treatment, the blood-vessel running-direction information image creating unit 345 creates a blood-vessel running-direction information image on which the two-dimensional blood-vessel core line projected from the three-dimensional blood-vessel core line is displayed in variation to indicate the blood-vessel running direction, based on positional information about the three-dimensional blood-vessel core line created by the three-dimensional blood-vessel core-line extracting unit 342. The blood-vessel running-direction information displayed X-ray image display unit 349 then displays onto the display unit 7 the blood-vessel running-direction information image created by the blood-vessel running-direction information image creating unit 345 in a superimposed manner over the X-ray image.

Thus, according to the third embodiment, as information that indicates the blood-vessel running direction is provided, an operator can easily determine an appropriate direction of turning the guide wire. Moreover, the operator can smoothly move the guide wire along the blood-vessel running direction, so that reduction in operation time and improvement in precision can be achieved.

Furthermore, according to the third embodiment, the guide-wire position sensor 310 detects the head position and the head direction of the guide wire inserted into the blood vessel. The blood-vessel running-direction information image creating unit 345 then creates the graphic image 15 that indicates the blood-vessel running direction at the guide-wire head position based on the head position and the head direction of the guide wire detected by the guide-wire position sensor 310 and positional information about the three-dimensional blood-vessel core line, and superimposes the created graphic image 15 over the blood-vessel running-direction information image. Thus, according to the third embodiment, the operator can easily grasp to which direction the blood vessel turns ahead of movement of the guide wire.

Moreover, according to the third embodiment, the guide-wire directional-information image creating unit 346 creates the graphic image 16 that indicates the head direction of the guide-wire based on the head position and the head direction of the guide wire detected by the guide-wire position sensor 310, the blood-vessel running-direction information displayed X-ray image display unit 349 then displays the graphic image 16 created by the guide-wire directional-information image creating unit 346 further over the X-ray image in a superimposed manner. Thus, according to the third embodiment, the operator can easily grasp toward which direction the head of the guide wire moves inside the blood vessel.

Furthermore, according to the third embodiment, the directional-difference calculation/warning determination unit 344 calculates a relative angle between the head direction of the guide wire and the blood-vessel running direction at the guide-wire head position based on the positional information about the three-dimensional blood-vessel core line created by the three-dimensional blood-vessel core-line extracting unit 342 and the head position and the head direction of the guide wire detected by the guide-wire position sensor 310, and determines whether the calculated relative angle exceeds a predetermined threshold value. If the directional-difference calculation/warning determination unit 344 determines that the relative angle exceeds the threshold value, the alarm-indication image creating unit 347 creates an alarm indication image, and the alarm output unit 320 outputs an alarm. Thus, according to the third embodiment, it is configured to ensure that when the moving direction of the guide wire largely departs from the blood-vessel running direction, the operator notices that the guide wire needs to be turned.

Although the case where an blood-vessel running-direction information image is displayed in a superimposed manner over an X-ray image is explained in the third embodiment, if a blood vessel to be performed with treatment has a complex shape, the X-ray image may be sometimes difficult to see due to the blood-vessel running-direction information image in some cases. Therefore, a fourth embodiment according to the present invention is explained in a case where an image that blood-vessel running-direction information is superimposed over an MIP image of three-dimensional volume data is created, and the created image is displayed in parallel with an X-ray image.

Figure 20:
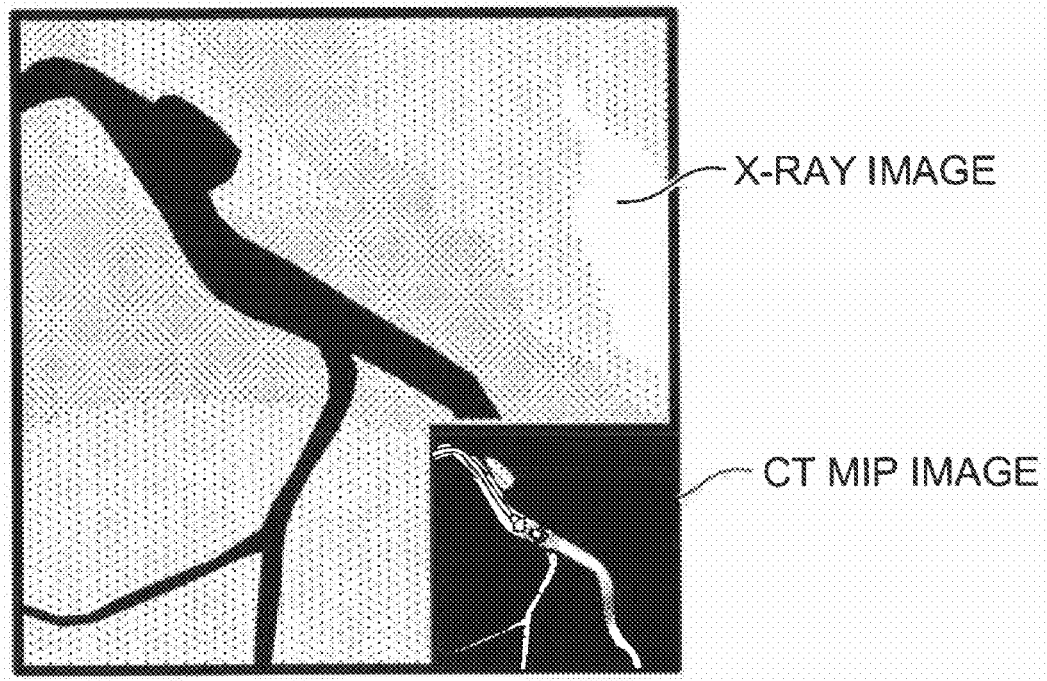
FIG. 20 is a schematic diagram for explaining a concept of blood-vessel running-direction information display performed by an X-ray angiographic apparatus according to a fourth embodiment of the present invention.

First of all, a concept of displaying blood-vessel running-direction information performed by an X-ray angiographic apparatus according to the fourth embodiment is explained below. FIG. 20 is a schematic diagram for explaining the concept of displaying blood-vessel running-direction information performed by the X-ray angiographic apparatus according to the fourth embodiment. Compared with the X-ray angiographic apparatus according to the third embodiment that displays a blood-vessel running-direction information image over an X-ray image in a superimposed manner, the X-ray angiographic apparatus according to the fourth embodiment creates, as shown in the figure, an image that a blood-vessel running-direction information image is superimposed over an MIP image of three-dimensional volume data obtained from a CT image, reduces the created image in size, and displays it in parallel with the X-ray image.

In this way, the X-ray angiographic apparatus according to the fourth embodiment displays, during a PCI treatment, in parallel with an X-ray image, an MIP image over which a blood-vessel running-direction information image that display of a two-dimensional blood-vessel core line projected from a three-dimensional blood-vessel core line is changed to display a blood-vessel running direction is superimposed. Accordingly, the X-ray angiographic apparatus according to the fourth embodiment is configured such that as information indicating the blood-vessel running direction is provided without disturbing visibility of the X-ray image, an operator can easily determine an appropriate direction of turning the guide wire, even when the blood vessel to be performed with treatment has a complex shape.

A configuration of the X-ray angiographic apparatus according to the fourth embodiment is explained below. The configuration of the X-ray angiographic apparatus according to the fourth embodiment is basically the same as the configuration shown in FIG. 2, and only details of the image processing unit is different. Therefore, a configuration and a processing procedure of an image processing unit according to the fourth embodiment are explained below. For convenience of explanation, functional units that play roles similar to those of the units shown in FIG. 12 are assigned with the same reference numerals, and detailed explanations of them are omitted.

Figure 21:
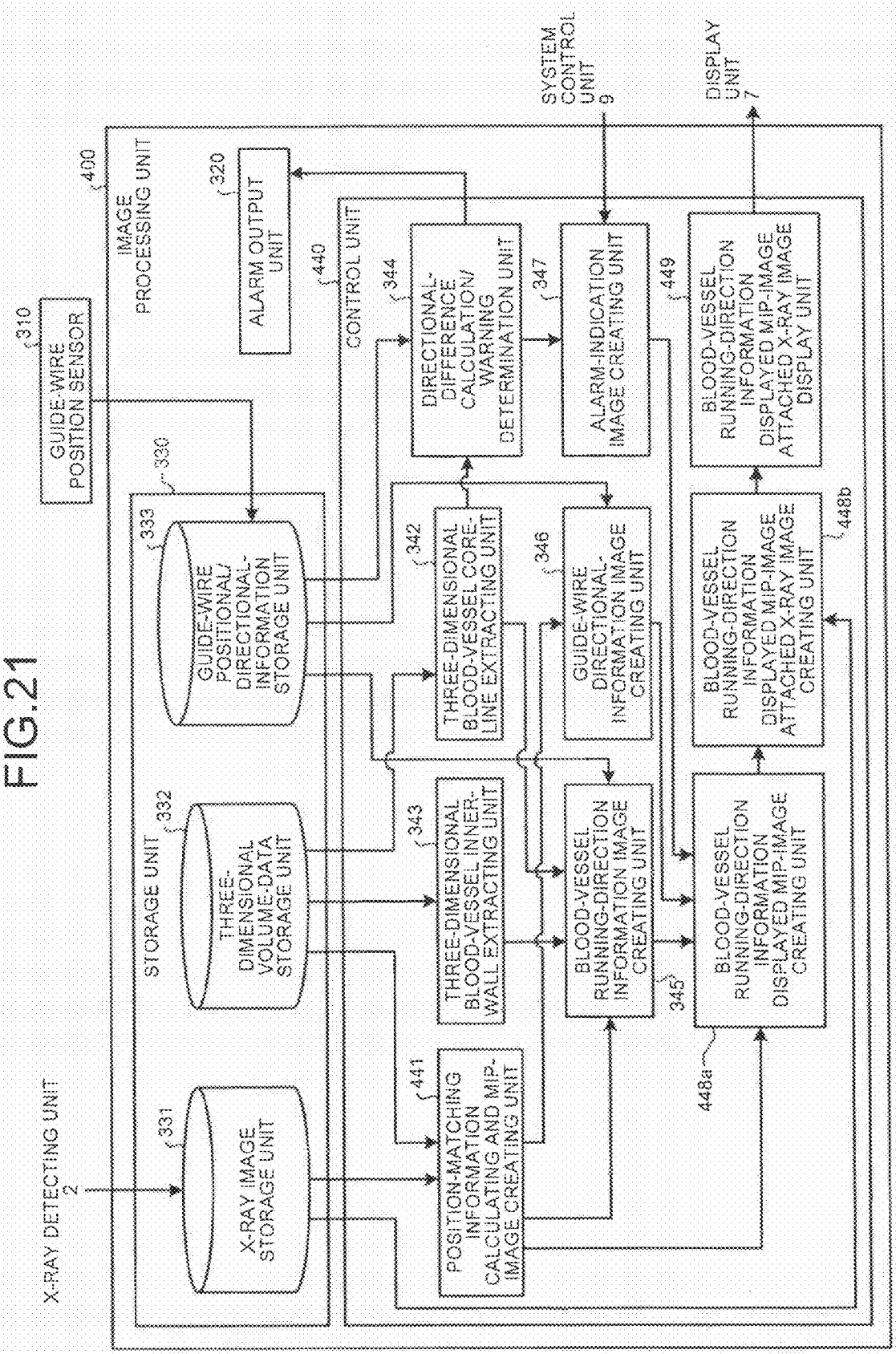
FIG. 21 is a functional block diagram of a configuration of an image processing unit according to the fourth embodiment.

FIG. 21 is a functional block diagram of the configuration of an image processing unit 400 according to the fourth embodiment. As shown in the figure, the image processing unit 400 includes the guide-wire position sensor 310, the alarm output unit 320, the storage unit 330, and a control unit 440.

The control unit 440 controls processing of X-ray image data received from the X-ray detecting unit 2, under the control of the system control unit 9. The control unit 440 includes a position-matching information calculating and MIP-image creating unit 441, the three-dimensional blood-vessel core-line extracting unit 342, the three-dimensional blood-vessel inner-wall extracting unit 343, the directional-difference calculation/warning determination unit 344, the blood-vessel running-direction information image creating unit 345, the guide-wire directional-information image creating unit 346, the alarm-indication image creating unit 347, a blood-vessel running-direction information displayed MIP-image creating unit 448a, a blood-vessel running-direction information displayed MIP-image attached X-ray image creating unit 448b, and a blood-vessel running-direction information displayed MIP-image attached X-ray image display unit 449.

The position-matching information calculating and MIP-image creating unit 441 acquires position-matching parameters from three-dimensional volume data stored in the three-dimensional volume-data storage unit 332, namely, the projection direction, the position, and the magnification, which are to be required for creating an image having the same projection direction, position, and magnification as those of an X-ray image stored in the X-ray image storage unit 331; and furthermore, creates an MIP image based on the acquired positional parameters.

For example, the position-matching information calculating and MIP-image creating unit 441 creates an MIP image by acquiring position-matching parameters according to the method similar to that of the position-matching information calculating unit 341 as explained in the third embodiment.

The blood-vessel running-direction information displayed MIP-image creating unit 448a creates, as a blood-vessel running-direction information displayed MIP-image, a two-dimensional image that the blood-vessel running-direction information image created by the blood-vessel running-direction information image creating unit 345, the guide-wire directional-information image created by the guide-wire directional-information image creating unit 346, and the alarm indication image created by the alarm-indication image creating unit 347 are superimposed over the MIP image created by the position-matching information calculating and MIP-image creating unit 441.

The blood-vessel running-direction information displayed MIP-image attached X-ray image creating unit 448*b* acquires an X-ray image stored in the X-ray image storage unit 331, and creates, as a blood-vessel running-direction information displayed MIP-image attached X-ray image, a two-dimensional image that the blood-vessel running-direction information displayed MIP-image created by the blood-vessel running-direction information displayed MIP-image creating unit 448*a* is reduced in size and arranged in parallel with the acquired X-ray image.

The blood-vessel running-direction information displayed MIP-image attached X-ray image display unit 449 displays the blood-vessel running-direction information displayed MIP-image attached X-ray image created by the blood-vessel running-direction information displayed MIP-image attached X-ray image creating unit 448*b* onto the display unit 7.

A processing procedure of the image processing unit 400 according to the fourth embodiment is explained below. FIG. 22 is a flowchart of the processing procedure of the image processing unit 400 according to the fourth embodiment. As shown in the figure, to begin with, the image processing unit 400 performs the processing similar to Step S301 shown in FIG. 19 prior to a PCI treatment (Step S401).

During the PCI treatment, the image processing unit 400 performs the processing similar to Steps S302 to S304 shown in FIG. 19 (Steps S402 to S404). Along with the above processing, the position-matching information calculating and MIP-image creating unit 441 creates an MIP image based on the position-matching parameters obtained from the three-dimensional volume data stored in the three-dimensional volume-data storage unit 332 (Step S405). Furthermore, the processing similar to Steps S305 to S307 shown in FIG. 19 is performed (Steps S406 to S408).

Subsequently, the blood-vessel running-direction information displayed MIP-image creating unit 448*a* creates a blood-vessel running-direction information displayed MIP-image that the blood-vessel running-direction information image created by the blood-vessel running-direction information image creating unit 345, the guide-wire directional-information image created by the guide-wire directional-information image creating unit 346, and the alarm indication image created by the alarm-indication image creating unit 347 are superimposed over the MIP image created by the position-matching information calculating and MIP-image creating unit 441 (Step S409).

After that, the blood-vessel running-direction information displayed MIP-image attached X-ray image creating unit 448*b* acquires an X-ray image stored in the X-ray image storage unit 331, and creates a blood-vessel running-direction information displayed MIP-image attached X-ray image that the blood-vessel running-direction information displayed MIP-image created by the blood-vessel running-direction information displayed MIP-image creating unit 448*a* is reduced in size and arranged in parallel with the acquired X-ray image (Step S410).

The blood-vessel running-direction information displayed MIP-image attached X-ray image display unit 449 then displays the blood-vessel running-direction information displayed MIP-image attached X-ray image created by the blood-vessel running-direction information displayed MIP-image attached X-ray image creating unit 448*b* onto the display unit 7 (Step S411).

As described above, according to the fourth embodiment, the position-matching information calculating and MIP-image creating unit 441 creates an MIP image of a blood vessel based on three-dimensional volume data. The blood-vessel running-direction information displayed MIP-image creating unit 448*a* creates a blood-vessel running-direction information displayed MIP-image that a blood-vessel running-direction information image created by the blood-vessel running-direction information image creating unit 345 is superimposed over a three-dimensional rendering image created by the position-matching information calculating and MIP-image creating unit 441.

The blood-vessel running-direction information displayed MIP-image attached X-ray image creating unit 448*b* creates a blood-vessel running-direction information displayed MIP-image attached X-ray image that the blood-vessel running-direction information displayed MIP-image created by the blood-vessel running-direction information displayed MIP-image creating unit 448*a* is reduced in size and arranged in parallel with an X-ray image. The blood-vessel running-direction information displayed MIP-image attached X-ray image display unit 449 then displays the blood-vessel running-direction information displayed MIP-image attached X-ray image created by the blood-vessel running-direction information displayed MIP-image attached X-ray image creating unit 448*b* onto the display unit 7.

Thus, according to the fourth embodiment, as information indicating the blood-vessel running direction is provided without disturbing visibility of the X-ray image, an operator can easily determine an appropriate direction of turning the guide wire, even when the blood vessel to be performed with treatment has a complex shape.

Although the first and third embodiments are explained above in the case where the position-matching information calculating unit 125 or 341 acquires position-matching parameters (projection direction, position, and magnification) from the system control unit 9, a method of acquiring position-matching parameters is not limited to this, but also other general methods can be used. Another method of acquiring position-matching parameters is explained below; however, a positioning algorithm described below is an example, and other general methods can be used.

For example, when position-matching parameters cannot be acquired from the system control unit 9, it can be configured such that a user sets a projection direction by using a certain user interface, and a position and a magnification are to be calculated based on the projection direction.

Figure 23A:
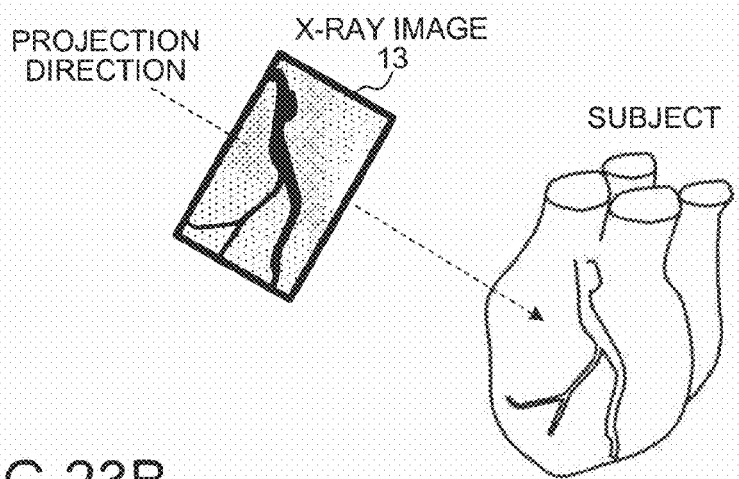
FIGS. 23A and 23B are schematic diagrams illustrating an example of a user interface for setting a projection direction.
Figure 23B:
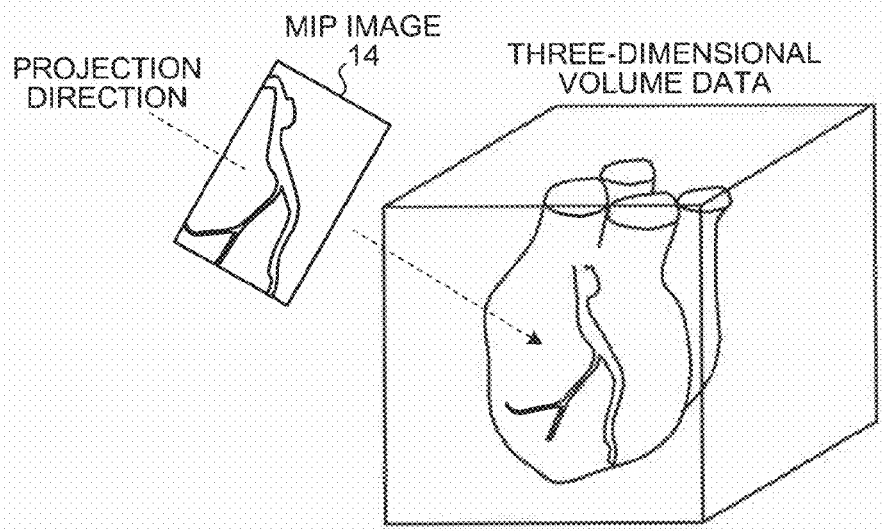

FIGS. 23A and 23B are schematic diagrams that depict an example of a user interface for setting a projection direction. For example, the position-matching information calculating unit 125 or 341 displays an X-ray image 13 onto the display unit 7 as shown in FIG. 23A, further displays an MIP image 14 onto the display unit 7 as shown FIG. 23B, and receives an operation to the MIP image 14 from the user via the operation unit 8, such as a mouse.

When the user drags the MIP image 14 by using a mouse or another interface, the position-matching information calculating unit 125 or 341 performs rendering in accordance with the user's operation, and turns the MIP image 14. Accordingly, the user sets the projection direction of the MIP image 14 by turning the MIP image 14 to be displayed in the same projection direction as that of the X-ray image 13.

After the projection direction of the MIP image 14 is set by the user, the position-matching information calculating unit 125 or 341 sets the position and the magnification of the MIP image 14 in accordance with the X-ray image 13. Specifically, to begin with, the X-ray image is binarized based on brightness values into a contrasted blood-vessel area expressed by 1, and the other area expressed by 0. As a threshold value when binarizing into the two areas, for example, when the range of the brightness values is from 0 to 255, an area of which brightness value is less than 128 is the value 1 (the contrasted blood-vessel area), and an area of which brightness value is equal to or more than 128 is the value 0 (the other area).

Figure 24:
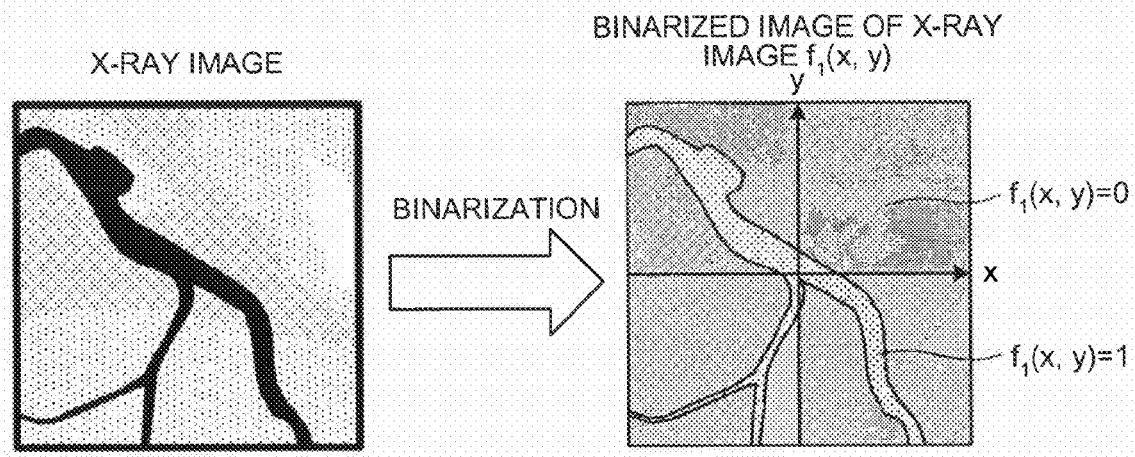
FIG. 24 is a schematic diagram for explaining binarization of an X-ray image.

It is assumed that the binarized X-ray image is represented by $f_1(x, y)$. FIG. 24 is a schematic diagram for explaining binarization of an X-ray image. As shown in the figure, where an X-ray image is represented by $f_1(x, y)$, the contrasted blood-vessel area is expressed by $f_1(x, y)=1$, and the other area is expressed by $f_1(x, y)=0$.

Subsequently, the position-matching information calculating unit 125 or 341 creates an MIP image when three-dimensional volume data is projected in the projection direction set by the user, and binarizes the created MIP image similarly to the X-ray image. As a threshold value when binarizing into the two areas, for example, an area of which CT value is equal to more than 128 is the value 1 (the contrasted blood-vessel area), and an area of which CT value is less than 128 is the value 0 (the other area). Suppose the binarized MIP image is represented by $f_2(x, y)$.

Subsequently, the position-matching information calculating unit 125 or 341 calculates a parallel movement amount and a magnification for position-matching the binarized image of the X-ray image $f_1(x, y)$ and the binarized image of the MIP image $f_2(x, y)$. A correlation function between $f_1(x, y)$ and $f_2(x, y)$ is expressed by Equation (4) as follows:

$$r(l, m, s) = \frac{1}{N^2} \sum_{x=-N/2}^{N/2-1} \sum_{y=-N/2}^{N/2-1} f_1(x, y) \cdot f_2((x+l)/s, (y+m)/s) \quad (4)$$

A combination of (l, m, s) that takes the maximum of r(l, m, s) according to the correlation function, namely, $(l_1, m_1, s_1)$, is to be calculated, and the binarized image of the MIP image $f_2(x, y)$ is to be magnified by $s_1$ times as $(l_1, m_1)$ is an origin, so that the binarized image of the MIP image $f_2(x, y)$ can be matched in position with the binarized image of the X-ray image $f_1(x, y)$. The position-matching information calculating unit 125 or 341 calculates the parallel movement amount and the magnification of the MIP image by performing the above calculation.

As described above by determining the projection direction, the parallel movement amount, and the magnification of the MIP image, the position-matching information calculating unit 125 or 341 can calculate the position-matching parameters, namely, the projection direction, the position, and the magnification, which are parameters to be required for creating an image having the same projection direction, position, and magnification as those of the X-ray image.

Although the fourth embodiment is explained above in the case where the user manually sets the projection direction, a variable that represents the projection direction can be added to the variables in Expression (4), so that the correlation function can be expanded to include the projection direction. In such case, the projection direction is also determined by binarization, time and efforts to set a projection direction manually by a user can be omitted.

Alternatively, it can be configured such that the position-matching information calculating unit 125 or 341 calculates the position-matching parameters by creating two-dimensional blood-vessel core-line data from the X-ray image, and further performing non-linear position-matching between the created two-dimensional blood-vessel core-line data and two-dimensional projection data of three-dimensional blood-vessel core-line data extracted by the three-dimensional blood-vessel core-line extracting unit 121 or 342. Accordingly, accuracy in synthesis of the X-ray image and the plaque-depth information image performed by the plaque-depth information image creating unit 126, and accuracy in synthesis of the X-ray image and the blood-vessel running-direction information image performed by the blood-vessel running-direction information displayed X-ray image creating unit 348 can be increased.

Alternatively, it can be configured such that after collecting a plurality of pieces of volume data per heartbeat in time sequence from an X-ray CT apparatus and storing them into the three-dimensional volume-data storage unit 111 or 332, a procedure from Step S101 to Step S104 shown in FIG. 7 or a procedure at Step S301 shown in FIG. 10 is performed on each piece of the volume data, and volume data at the same phase as the heartbeat phase when collecting the X-ray image is selected from among the pieces of the volume data, and subjected to position matching by the position-matching information calculating unit 125 or 341. Accordingly, accuracy in synthesis of the X-ray image and the plaque-depth information image performed by the plaque-depth information image creating unit 126, and accuracy in synthesis of the X-ray image and the blood-vessel running-direction information image performed by the blood-vessel running-direction information displayed X-ray image creating unit 348 can be further increased.

The second and fourth embodiments can be configured such that the position-matching information calculating and MIP-image creating unit 225 or 441 acquires position-matching parameters according to the method explained above.

The first to fourth embodiments are explained above in the case where the X-ray angiographic apparatus displays either information indicating the position of a blood-vessel lesion-site (plaque) in the depth direction or information indicating the blood-vessel running direction. However, the present invention is not limited to these. For example, it can be configured to display the plaque-depth information image and the blood-vessel running-direction information image in parallel with the X-ray image.

Figure 25:
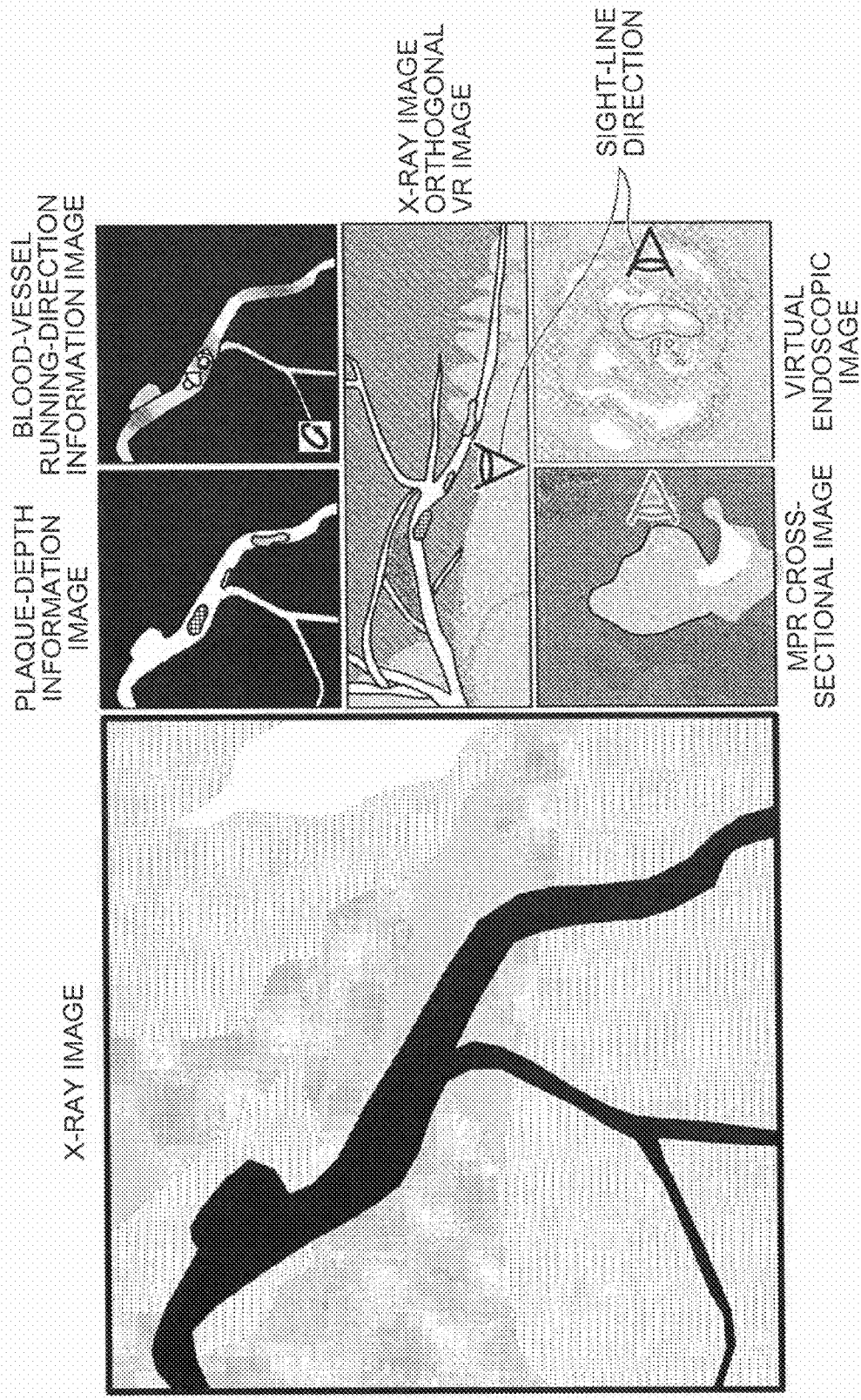
FIG. 25 is a schematic diagram illustrating an example of screen display when displaying an orthogonal image.
Figure 26:
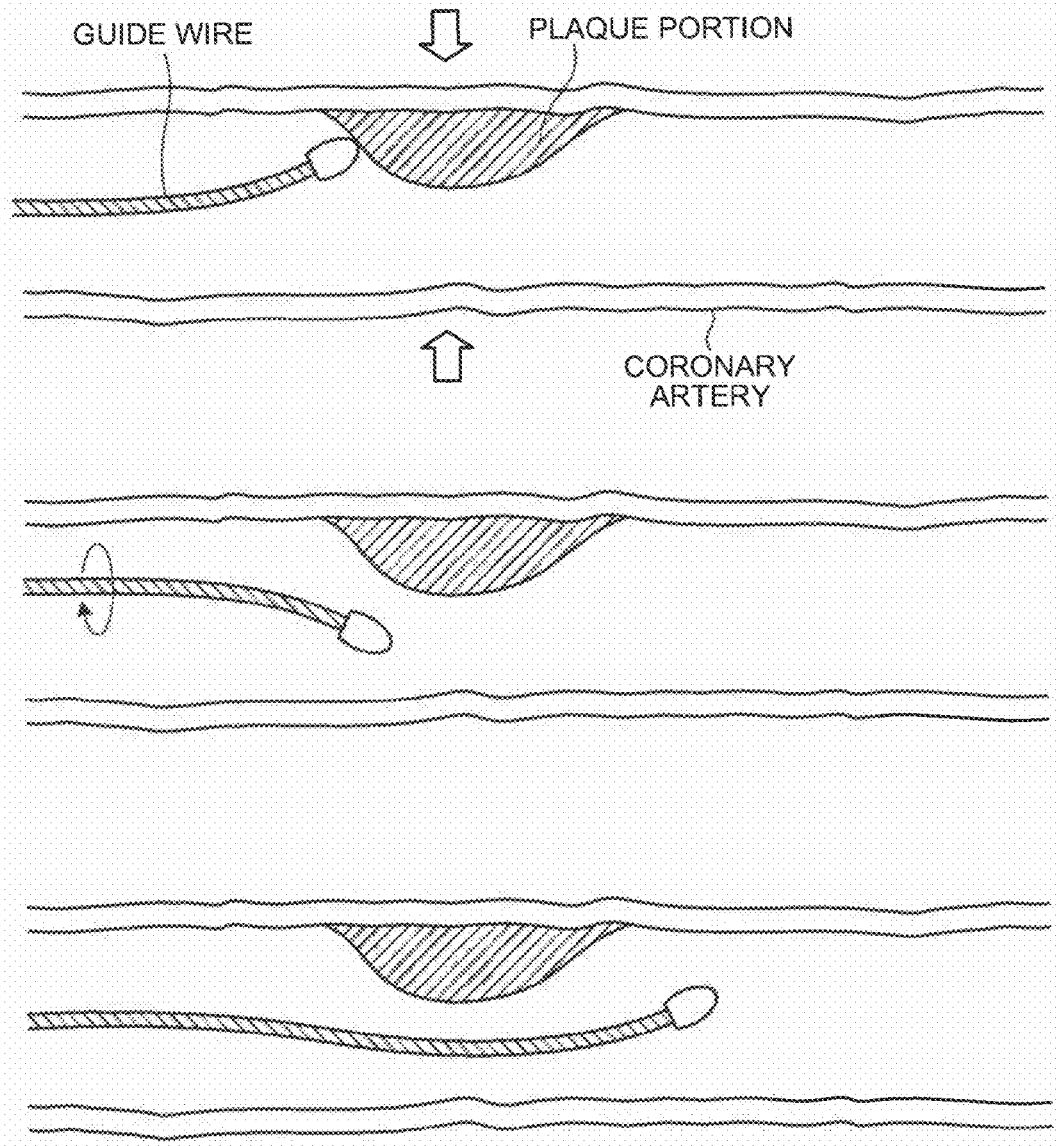
FIG. 26 is a schematic diagram for explaining relation between the direction of a guide wire and a coarctation.
Figure 27:
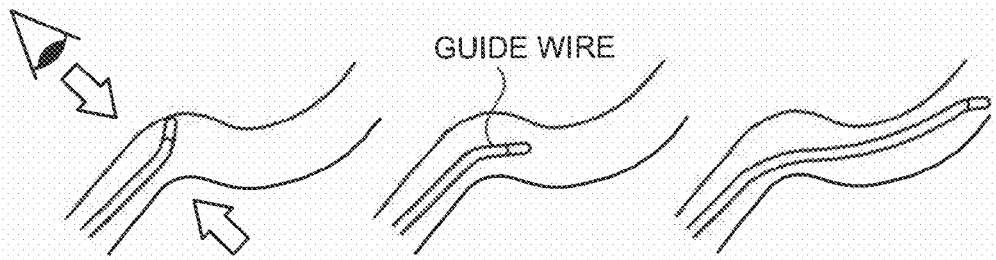
FIG. 27 is a schematic diagram for explaining relation between the direction of the guide wire and the running direction of a blood vessel.

Moreover, for example, the X-ray angiographic apparatus can be configured to include an orthogonal-image creating unit that creates as an orthogonal image a cross-sectional image or a three-dimensional rendering image that is orthogonal to the three-dimensional blood-vessel core line or the X-ray image, and to display the orthogonal image created by the orthogonal-image creating unit in parallel with the X-ray image. FIG. 25 is a schematic diagram that depicts an example of screen display when displaying an orthogonal image.

For example, the orthogonal-image creating unit creates, as orthogonal images, a Multi-Planar Reconstruction (MPR) cross-sectional image which is orthogonal to the blood-vessel core line at the guide-wire head position, a Virtual Endoscopic (VE) Image, and an X-ray image orthogonal Volume Rendering (VR) image that is a VR image orthogonal to the X-ray image, based on three-dimensional volume data stored in the three-dimensional volume-data storage unit 111 or 332.

The plaque-depth information superimposed X-ray image display unit 128, the plaque-depth information superimposed MIP-image attached X-ray image display unit 228, the blood-vessel running-direction information displayed X-ray image display unit 349, or the blood-vessel running-direction information displayed MIP-image attached X-ray image display unit 449, for example, then displays each of the orthogonal images created by the orthogonal-image creating unit in parallel with the X-ray image together with the plaque-depth information image and the blood-vessel running-direction information image, as shown in FIG. 25.

The same plaque as the plaque displayed on the plaque-depth information image is displayed on the X-ray image orthogonal VR image in the figure, the plaques corresponding to each other between the both images are colored in the same color. As shown in the figure, a mark imitating an eye displayed on the MPR cross-sectional image, the virtual endoscopic image, and the X-ray image orthogonal VR image (shown as a sight-line direction in the figure) indicates the projection direction of the X-ray image with the sight-line direction of the eye.

In this way, as the X-ray angiographic apparatus displays the cross-sectional image or the three-dimensional rendering image that is orthogonal to the three-dimensional blood-vessel core line or the X-ray image as an orthogonal image, even when the operator cannot distinguish whether a relevant portion is shallow or deep in the X-ray image based on a color difference, the operator can easily grasp a position in the depth direction by referring to the orthogonal image.

The X-ray angiographic apparatus can also be configured to receive a request to switch display from a user via the operation unit, and to switch displays of the plaque-depth information image and the blood-vessel running-direction information image in accordance with the received request. Accordingly, during treatment, the operator can appropriately obtain information for determining a turning direction of the guide wire in accordance with a shape and a direction of a blood vessel at the guide-wire head position.

Although the second and fourth embodiments are explained above in the case of using an MIP image, the present invention is not limited to this, and another three-dimensional rendering image, for example, an Average Intensity Projection (AvIP), or a VR image can be used.

Although the first to fourth embodiments are explained above in the case where three-dimensional volume data of an image of a heart area imaged by an X-ray CT apparatus, the present invention is not limited to this, and three-dimensional volume data of an image taken by another medical diagnostic imaging apparatus, such as an X-ray diagnostic apparatus, or a Magnetic Resonance Imaging (MRI) apparatus can be used.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray imaging apparatus comprising:
   an X-ray image taking unit that takes an X-ray image by irradiating an X-ray to a subject and detecting the X-ray passed through the subject;
   a three-dimensional blood-vessel information creating unit that creates information concerning positions of a three-dimensional blood-vessel core line and a blood-vessel lesion-site inside a blood vessel to be imaged, based on three-dimensional volume data obtained from an image taken by a medical diagnostic imaging apparatus;
   a blood-vessel lesion-site-depth information image creating unit that creates a blood-vessel lesion-site-depth information image in which a display pattern of a blood-vessel lesion-site is changed in accordance with whether the blood-vessel lesion-site is present in front of or in the back of a three-dimensional blood-vessel core line, based on the information concerning positions of the three-dimensional blood-vessel core line and the blood-vessel lesion-site created by the three-dimensional blood-vessel-information creating unit; and
   an X-ray image display unit that displays the blood-vessel lesion-site-depth information image created by the blood-vessel lesion-site-depth information image creating unit in a superimposed manner over the X-ray image.

2. The apparatus according to claim 1, wherein the X-ray image display unit displays the blood-vessel lesion-site-depth information image in a superimposed manner over the X-ray image, after acquiring information concerning a projection direction, a position and a magnification ratio of the blood vessel, and matching the position of the blood vessel based on the acquired information.

3. The apparatus according to claim 2, further comprising:
   a projection-direction setting unit that sets a projection direction of the blood vessel based on an operation by a user, wherein
   the X-ray image display unit acquires the information concerning the position and the magnification ratio based on the projection direction set by the projection-direction setting unit.

4. The apparatus according to claim 1, further comprising:
   a rendering-image creating unit that creates a three-dimensional rendering image of the blood vessel, and creates a depth information attached rendering image by superimposing the blood-vessel lesion-site-depth information image created by the blood-vessel lesion-site-depth information image creating unit over the created three-dimensional rendering image, wherein
   the X-ray image display unit displays the depth information attached rendering image created by the rendering image creating unit in parallel with the X-ray image.

5. The apparatus according to claim 1, further comprising:
   an orthogonal-image creating unit that creates as an orthogonal image any one of a cross-sectional image and a three-dimensional rendering image that is orthogonal to any one of the three-dimensional blood-vessel core line and the X-ray image, based on the three-dimensional volume data, wherein
   the X-ray image display unit displays the orthogonal image created by the orthogonal-image creating unit in parallel with the X-ray image.

6. An image processing display apparatus comprising:
   a three-dimensional blood-vessel information creating unit that creates information concerning positions of a three-dimensional blood-vessel core line and a blood-vessel lesion-site inside a blood vessel to be imaged, based on three-dimensional volume data obtained from an image taken by a medical diagnostic imaging apparatus;
   a blood-vessel lesion-site-depth information image creating unit that creates a blood-vessel lesion-site-depth information image in which a display pattern of a blood-vessel lesion-site is changed in accordance with whether the blood-vessel lesion-site is present in front of or in the back of a three-dimensional blood-vessel core line, based on the information concerning positions of the three-dimensional blood-vessel core line and the blood-vessel lesion-site created by the three-dimensional blood-vessel-information creating unit; and an X-ray image display unit that displays the blood-vessel lesion-site-depth information image created by the blood-vessel lesion-site-depth information image creating unit in a superimposed manner over an X-ray image taken by an X-ray image taking unit.

7. A computer program product having a computer readable medium including programmed instructions for performing an image processing and image display, wherein the instructions, when executed by a computer, cause the computer to perform:
creating information concerning positions of a three-dimensional blood-vessel core line and a blood-vessel lesion-site inside a blood vessel to be imaged, based on three-dimensional volume data obtained from an image taken by a medical diagnostic imaging apparatus;
creating a blood-vessel lesion-site-depth information image in which a display pattern of a blood-vessel lesion-site is changed in accordance with whether the blood-vessel lesion-site is present in front of or in the back of a three-dimensional blood-vessel core line, based on the created information concerning positions of the three-dimensional blood-vessel core line and the blood-vessel lesion-site; and
displaying on a display unit the created blood-vessel lesion-site-depth information image in a superimposed manner over an X-ray image taken by an X-ray image taking unit.

8. An X-ray imaging apparatus comprising:
an X-ray image taking unit that takes an X-ray image by irradiating an X-ray to a subject and detecting X-ray passed through the subject;
a three-dimensional blood-vessel core-line creating unit that creates a three-dimensional blood-vessel core line representing a core line of a blood vessel to be imaged, based on three-dimensional volume data obtained from an image taken by a medical diagnostic imaging apparatus;
a blood-vessel running-direction information image creating unit that creates a blood-vessel running-direction information image in which a display pattern of a blood vessel is changed so as to display a running direction of the blood vessel, based on positional information concerning the three-dimensional blood-vessel core line created by the three-dimensional blood-vessel core-line creating unit; and
an X-ray image display unit that displays the blood-vessel running-direction information image created by the blood-vessel running-direction information image creating unit in a superimposed manner over the X-ray image.

9. The apparatus according to claim 8, wherein the blood-vessel running-direction information image creating unit changes a display pattern of the blood vessel on the blood-vessel running-direction information image in accordance with a position of the three-dimensional blood-vessel core line along a projection direction.

10. The apparatus according to claim 8, wherein the blood-vessel running-direction information image creating unit changes a display pattern of the blood vessel on the blood-vessel running-direction information image in accordance with an inclination of the three-dimensional blood-vessel core line with respect to a projection direction.

11. The apparatus according to claim 8, wherein the blood-vessel running-direction information image creating unit changes a display pattern of the blood vessel on the blood-vessel running-direction information image in accordance with a curvature ratio of the three-dimensional blood-vessel core line.

12. The apparatus according to claim 8, further comprising:
a linear-structure position detecting unit that detects a head position and a head direction of a linear structure inserted into the blood vessel, wherein
the blood-vessel running-direction information image creating unit creates a graphic that represents a running direction of the blood vessel at the head position of the linear structure, based on the head position and the head direction of the linear structure detected by the linear-structure position detecting unit and the positional information concerning the three-dimensional blood-vessel core line, and superimposes the created image over the blood-vessel running-direction information image.

13. The apparatus according to claim 8, further comprising:
a position-matching information calculating unit that calculates a projection direction, a position, and a magnification with respect to the subject by performing position-matching between a two-dimensional image created based on the three-dimensional volume data and the X-ray image, wherein
the X-ray image display unit superimposes the blood-vessel running-direction information image over the X-ray image after performing position-matching based on the projection direction, the position, and the magnification calculated by the position-matching information calculating unit, when displaying the blood-vessel running-direction information image on the X-ray image.

14. The apparatus according to claim 8, further comprising:
a rendering-image creating unit that creates a three-dimensional rendering image based on the three-dimensional volume data; and
a blood-vessel running-direction displayed rendering-image creating unit that creates a blood-vessel running-direction displayed rendering image in which the blood-vessel running-direction information image created by the blood-vessel running-direction information image creating unit is superimposed over the three-dimensional rendering image created by the rendering-image creating unit, wherein
the X-ray image display unit displays the blood-vessel running-direction displayed rendering image created by the blood-vessel running-direction displayed rendering-image creating unit in parallel with the X-ray image.

15. The apparatus according to claim 12, further comprising:
a linear-structure directional-information image creating unit that creates a graphic representing a head direction of the linear structure, based on the head position and the head direction of the linear structure detected by the linear-structure position detecting unit, wherein
the X-ray image display unit further displays the image created by the linear-structure directional-information image creating unit in a superimposed manner over the X-ray image.

16. The apparatus according to claim 12, further comprising:
a determining unit that calculates a relative angle between the running direction of the blood vessel at the head position of the linear structure and the head direction of the linear structure, and determines whether the calculated relative angle exceeds a predetermined threshold value, based on the positional information concerning the three-dimensional blood-vessel core line created by the three-dimensional blood-vessel core-line creating unit and the head position and the head direction of the linear structure detected by the linear-structure position detecting unit; and an alarm output unit that outputs an alarm when the determining unit determines that the relative angle exceeds the threshold value.

17. The apparatus according to claim 12, further comprising:
a position-matching information calculating unit that calculates a projection direction, a position, and a magnification with respect to the subject by performing position-matching between a two-dimensional image created based on the three-dimensional volume data and the X-ray image, wherein
the X-ray image display unit superimposes the blood-vessel running-direction information image over the X-ray image after performing position-matching based on the projection direction, the position, and the magnification calculated by the position-matching information calculating unit, when displaying the blood-vessel running-direction information image on the X-ray image.

18. The apparatus according to claim 12, further comprising:
a rendering-image creating unit that creates a three-dimensional rendering image based on the three-dimensional volume data; and
a blood-vessel running-direction displayed rendering-image creating unit that creates a blood-vessel running-direction displayed rendering image in which the blood-vessel running-direction information image created by the blood-vessel running-direction information image creating unit is superimposed over the three-dimensional rendering image created by the rendering-image creating unit, wherein
the X-ray image display unit displays the blood-vessel running-direction displayed rendering image created by the blood-vessel running-direction displayed rendering-image creating unit in parallel with the X-ray image.

19. The apparatus according to claim 15, further comprising:
a determining unit that calculates a relative angle between the running direction of the blood vessel at the head position of the linear structure and the head direction of the linear structure, and determines whether the calculated relative angle exceeds a predetermined threshold value, based on the positional information concerning the three-dimensional blood-vessel core line created by the three-dimensional blood-vessel core-line creating unit and the head position and the head direction of the linear structure detected by the linear-structure position detecting unit; and
an alarm output unit that outputs an alarm when the determining unit determines that the relative angle exceeds the threshold value.

20. The apparatus according to claim 15, further comprising:
a position-matching information calculating unit that calculates a projection direction, a position, and a magnification with respect to the subject by performing position-matching between a two-dimensional image created based on the three-dimensional volume data and the X-ray image, wherein
the X-ray image display unit superimposes the blood-vessel running-direction information image over the X-ray image after performing position-matching based on the projection direction, the position, and the magnification calculated by the position-matching information calculating unit, when displaying the blood-vessel running-direction information image on the X-ray image.

21. The apparatus according to claim 15, further comprising:
a rendering-image creating unit that creates a three-dimensional rendering image based on the three-dimensional volume data; and
a blood-vessel running-direction displayed rendering-image creating unit that creates a blood-vessel running-direction displayed rendering image in which the blood-vessel running-direction information image created by the blood-vessel running-direction information image creating unit is superimposed over the three-dimensional rendering image created by the rendering-image creating unit, wherein
the X-ray image display unit displays the blood-vessel running-direction displayed rendering image created by the blood-vessel running-direction displayed rendering-image creating unit in parallel with the X-ray image.

22. The apparatus according to claim 16, further comprising:
a position-matching information calculating unit that calculates a projection direction, a position, and a magnification with respect to the subject by performing position-matching between a two-dimensional image created based on the three-dimensional volume data and the X-ray image, wherein
the X-ray image display unit superimposes the blood-vessel running-direction information image over the X-ray image after performing position-matching based on the projection direction, the position, and the magnification calculated by the position-matching information calculating unit, when displaying the blood-vessel running-direction information image on the X-ray image.

23. The apparatus according to claim 16, further comprising:
a rendering-image creating unit that creates a three-dimensional rendering image based on the three-dimensional volume data; and
a blood-vessel running-direction displayed rendering-image creating unit that creates a blood-vessel running-direction displayed rendering image in which the blood-vessel running-direction information image created by the blood-vessel running-direction information image creating unit is superimposed over the three-dimensional rendering image created by the rendering-image creating unit, wherein
the X-ray image display unit displays the blood-vessel running-direction displayed rendering image created by the blood-vessel running-direction displayed rendering-image creating unit in parallel with the X-ray image.

24. An image processing display apparatus comprising:
a three-dimensional blood-vessel core-line creating unit that creates a three-dimensional blood-vessel core line representing a core line of a blood vessel to be imaged, based on three-dimensional volume data obtained from an image imaged by a medical diagnostic imaging apparatus;
a blood-vessel running-direction information image creating unit that creates a blood-vessel running-direction information image in which a display pattern of a blood vessel is changed so as to display a running direction of the blood vessel, based on positional information concerning the three-dimensional blood-vessel core line created by the three-dimensional blood-vessel core-line creating unit; and an X-ray image display unit that displays the blood-vessel running-direction information image created by the blood-vessel running-direction information image creating unit in a superimposed manner over an X-ray image taken by an X-ray image taking unit.

25. A computer program product having a computer readable medium including programmed instructions for performing an image processing and image display, wherein the instructions, when executed by a computer, cause the computer to perform:

creating a three-dimensional blood-vessel core line representing a core line of a blood vessel to be imaged based on three-dimensional volume data obtained from an image taken by a medical diagnostic imaging apparatus;

creating a blood-vessel running-direction information image in which a display pattern of a blood vessel is changed so as to display a running direction of the blood vessel, based on positional information concerning the created three-dimensional blood-vessel core line; and displaying the created blood-vessel running-direction information image in a superimposed manner over an X-ray image.

* * * * *